US011192920B2

(12) United States Patent
Lee et al.

(10) Patent No.: US 11,192,920 B2
(45) Date of Patent: Dec. 7, 2021

(54) PEPTIDES FOR BINDING TO CD44V6 AND USE THEREOF

(71) Applicant: KYUNGPOOK NATIONAL UNIVERSITY INDUSTRY-ACADEMIC COOPERATION FOUNDATION, Daegu (KR)

(72) Inventors: Byung-Heon Lee, Daegu (KR); Fatima Khan, Daegu (KR)

(73) Assignee: KYUNGPOOK NATIONAL, UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 73 days.

(21) Appl. No.: 16/772,810

(22) PCT Filed: Dec. 17, 2018

(86) PCT No.: PCT/KR2018/016022
§ 371 (c)(1),
(2) Date: Jun. 15, 2020

(87) PCT Pub. No.: WO2019/117691
PCT Pub. Date: Jun. 20, 2019

(65) Prior Publication Data
US 2021/0163535 A1 Jun. 3, 2021

(30) Foreign Application Priority Data

Dec. 15, 2017 (KR) ........................ 10-2017-0173305
Dec. 14, 2018 (KR) ........................ 10-2018-0161981

(51) Int. Cl.
*C07K 7/06* (2006.01)
*A61P 35/04* (2006.01)
(Continued)

(52) U.S. Cl.
CPC ................ *C07K 7/06* (2013.01); *A61P 35/00* (2018.01); *A61P 35/04* (2018.01); *G01N 33/57492* (2013.01); *A61K 38/00* (2013.01)

(58) Field of Classification Search
None
See application file for complete search history.

(56) References Cited

U.S. PATENT DOCUMENTS

2018/0155394 A1   6/2018   Lee et al.
2018/0201651 A1   7/2018   Lee et al.

FOREIGN PATENT DOCUMENTS

KR   10-2008-0039929 A   5/2008
KR   10-2016-0104727 A   9/2016
(Continued)

OTHER PUBLICATIONS

International Search Report for PCT/KR2018/016022 dated Apr. 10, 2019 from Korean Intellectual Property Office.
(Continued)

*Primary Examiner* — Kevin S Orwig
*Assistant Examiner* — John Michael Cronin
(74) *Attorney, Agent, or Firm* — Revolution IP, PLLC

(57) ABSTRACT

The present invention relates to a peptide bound to CD44v6 and uses for inhibiting cancer metastasis using the same, and the peptide of the present invention specifically binds to CD44v6 and inhibits it, thereby inhibiting cancer cell migration and metastasis. The peptides of the present invention selected two peptides (v6Pep-1 and v6Pep-2) that bind well to cells with high expression of human CD44v6 protein using phage peptide display technology and it was confirmed that it interferes with the binding between c-Met and CD44v6 to inhibit cancer cell migration. The peptide of the present invention is relatively stable in serum and shows a high potential as an anticancer treatment agent that sup- (Continued)

presses metastasis due to the progression and migration of cancer in the future.

9 Claims, 17 Drawing Sheets

Specification includes a Sequence Listing.

(51) Int. Cl.
*A61P 35/00* (2006.01)
*G01N 33/574* (2006.01)
*A61K 38/00* (2006.01)

(56) References Cited

FOREIGN PATENT DOCUMENTS

| KR | 10-1741594 B1 | 5/2017 |
| KR | 10-1750549 B1 | 7/2017 |
| WO | 2009-007427 A2 | 1/2009 |

OTHER PUBLICATIONS

Matzke-Ogi, Alexandra et al., "Inhibition of Tumor Growth and Metastasis in Pancreatic Cancer Models by Interference With CD44v6 Signaling", Gastroenterology, 2016, vol. 150, No. 2, pp. 513-525.
Todaro, Matilde et al., "CD44v6 is a Marker of Constitutive and Reprogramming Cancer Stem Cells Driving Colon Cancer Metastasis", Cell Stem Cell. 2014, vol. 14, No. 3, pp. 342-356.
NCBI, GenBank accession No. KYK25351.1 (Mar. 22, 2016).
NCBI, GenBank accession No. KRY97216.1 (Nov. 24, 2015).
Ying Peng et al., "Targeting aggressive prostate cancer-associated CD44v6 using phage display selected peptides", Oncotarget, Oct. 17, 2017, vol. 8, No. 49, pp. 86747-86768.

[FIG. 1A]
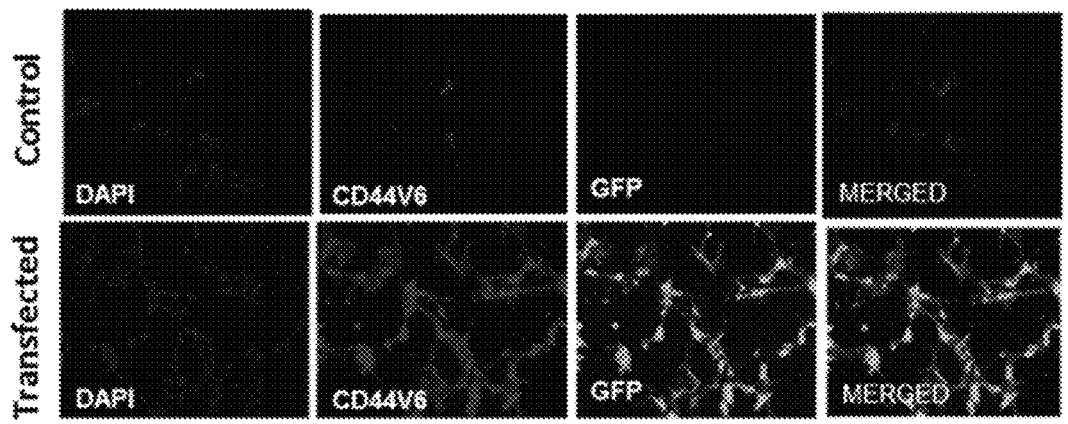
[FIG. 1B]
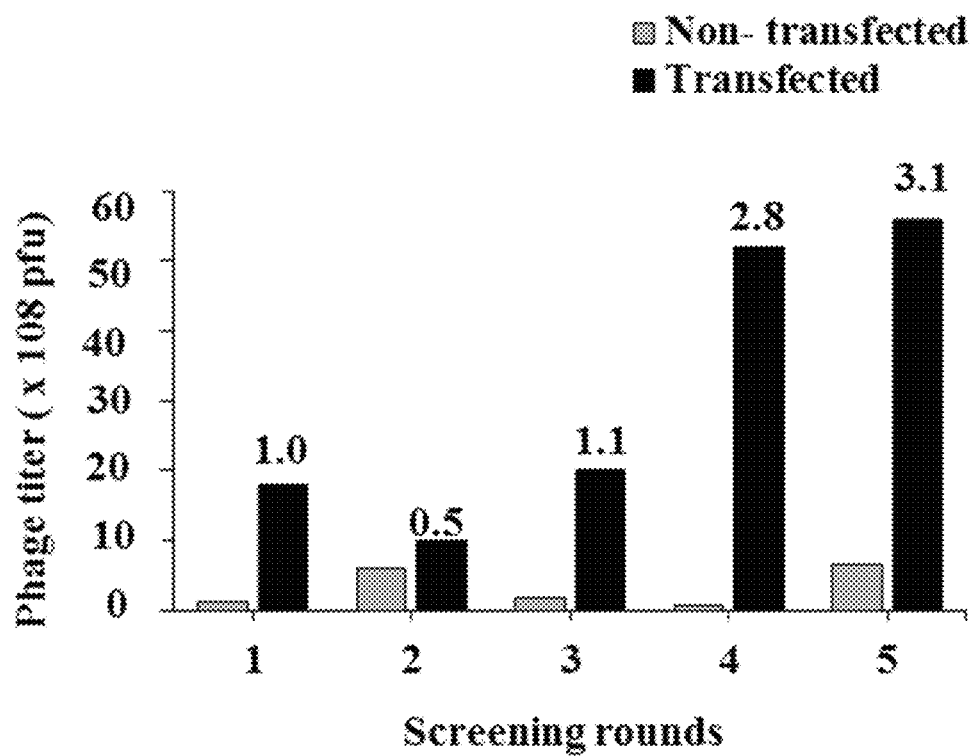

[FIG. 1C]
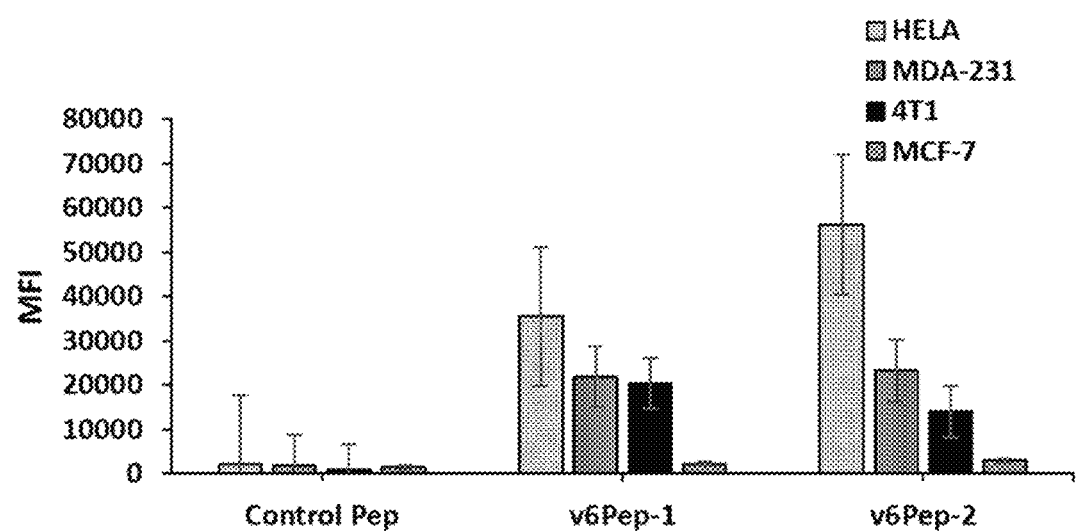

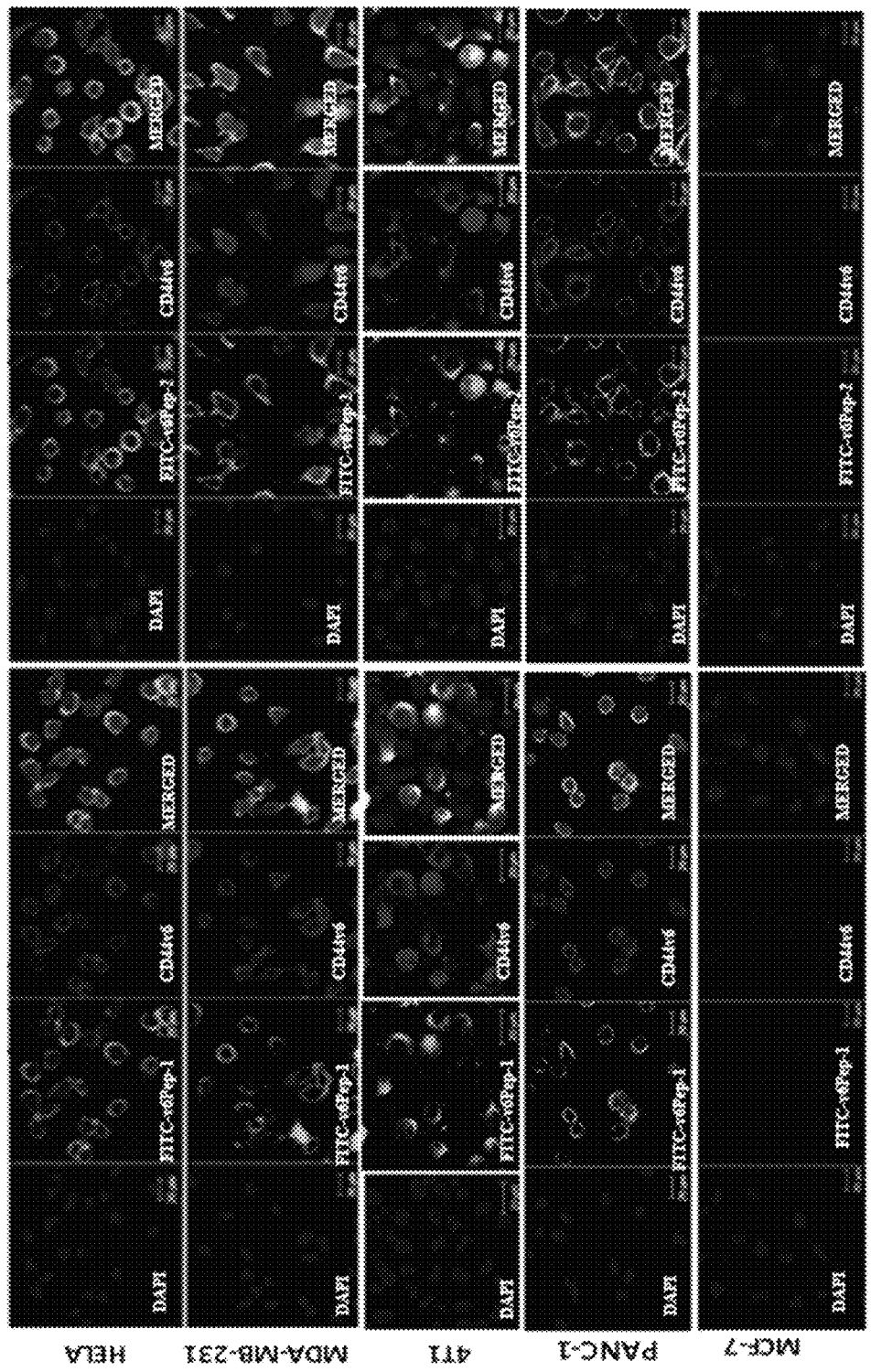
[FIG. 1D]

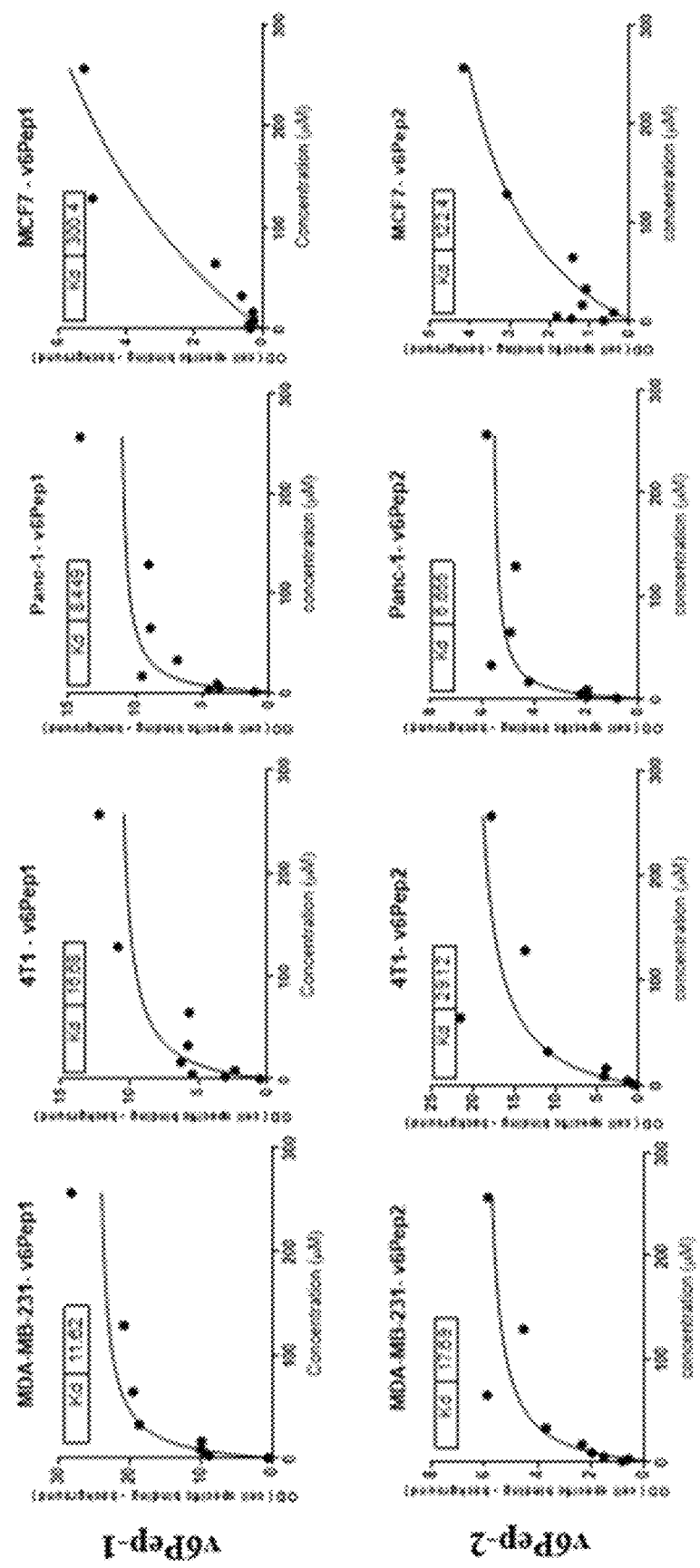
[FIG. 1E]

[FIG. 2A]
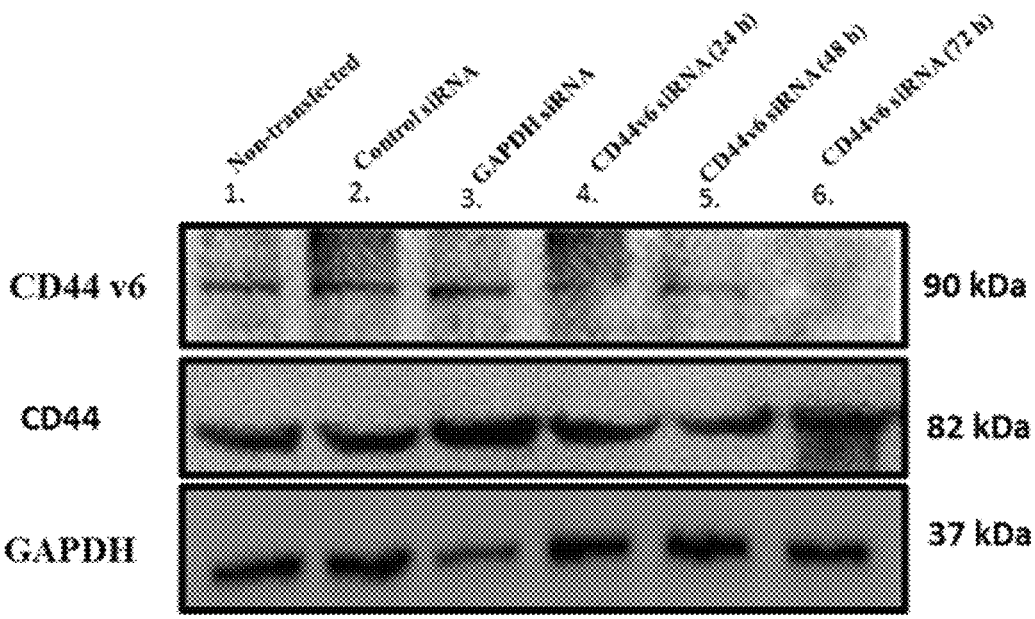
[FIG. 2B]
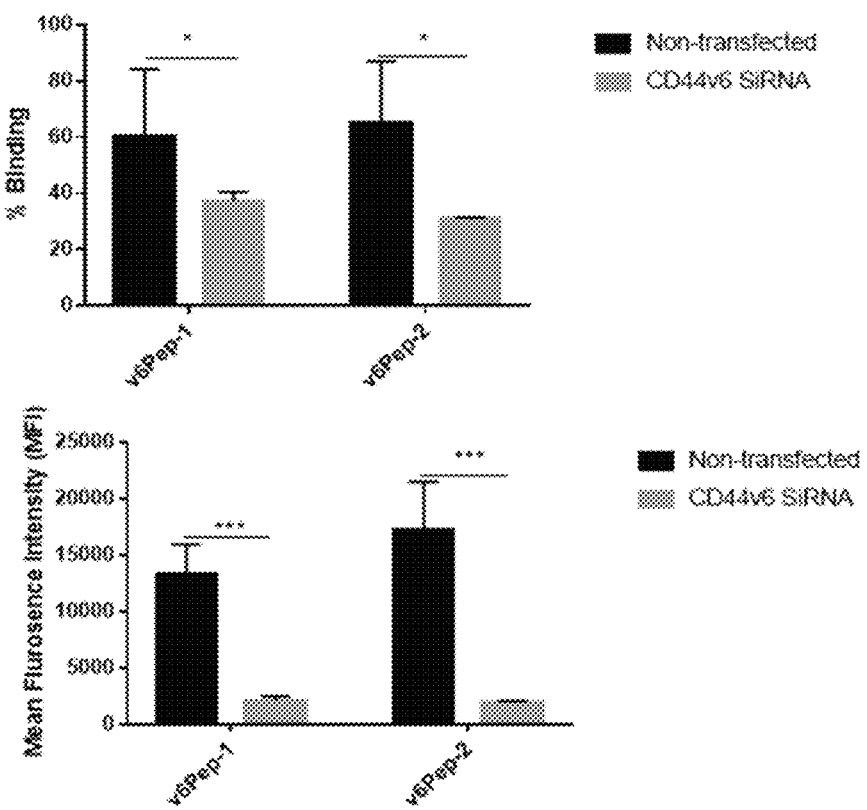

[FIG. 2C]
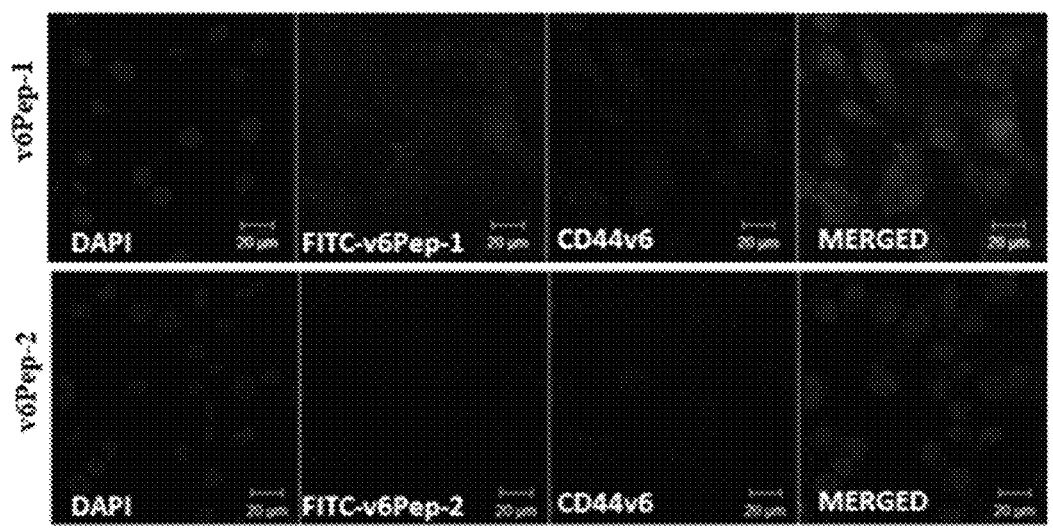
[FIG. 2D]
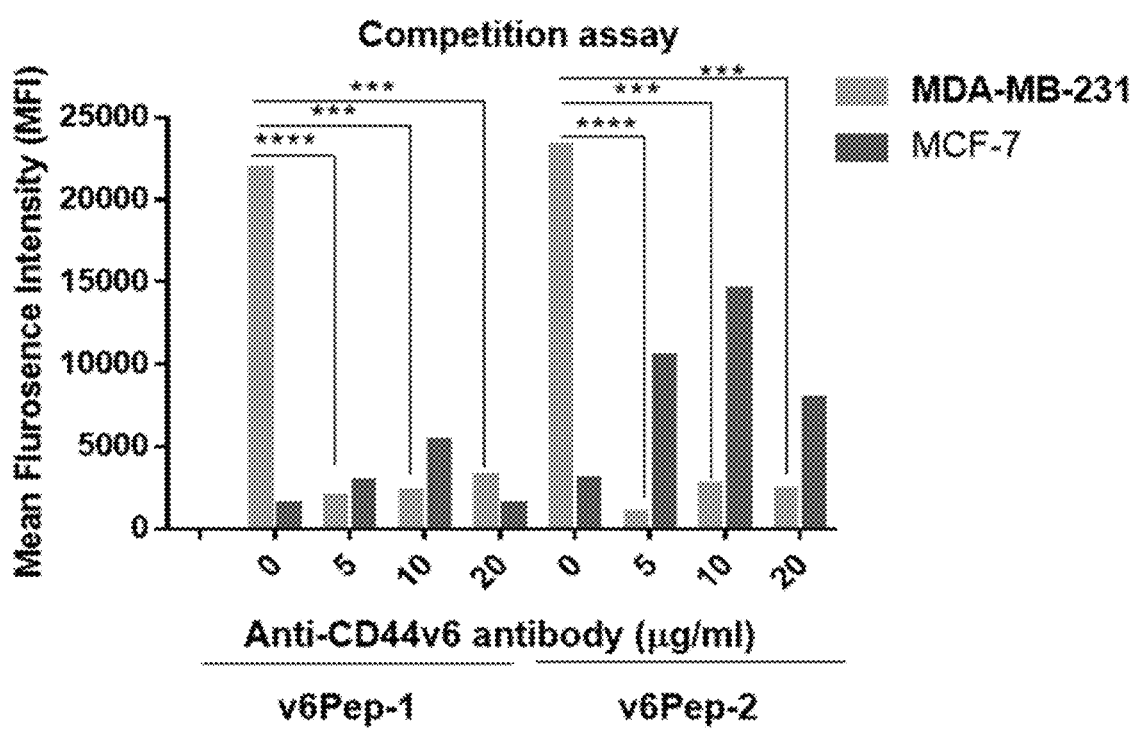

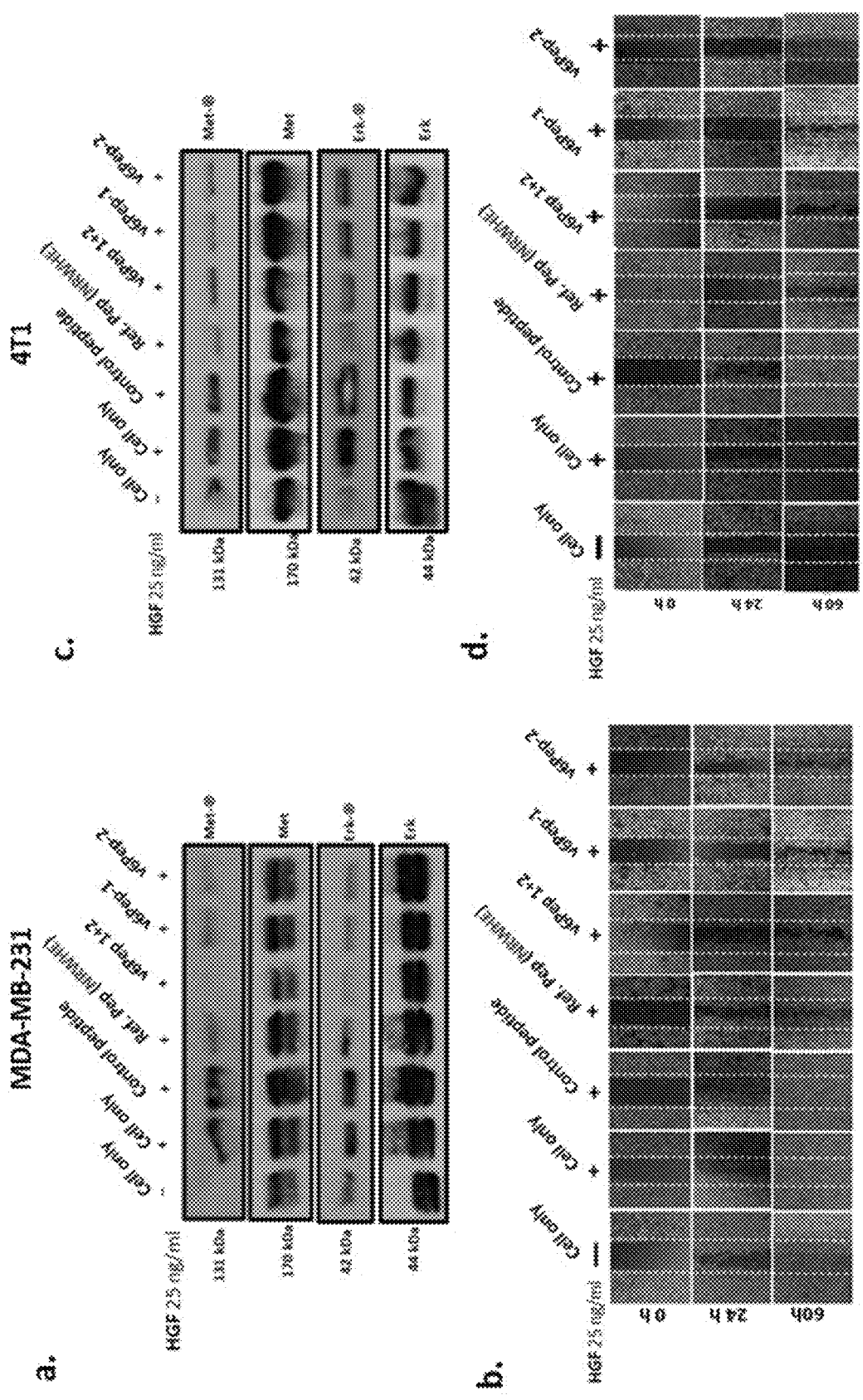
[FIG. 3]

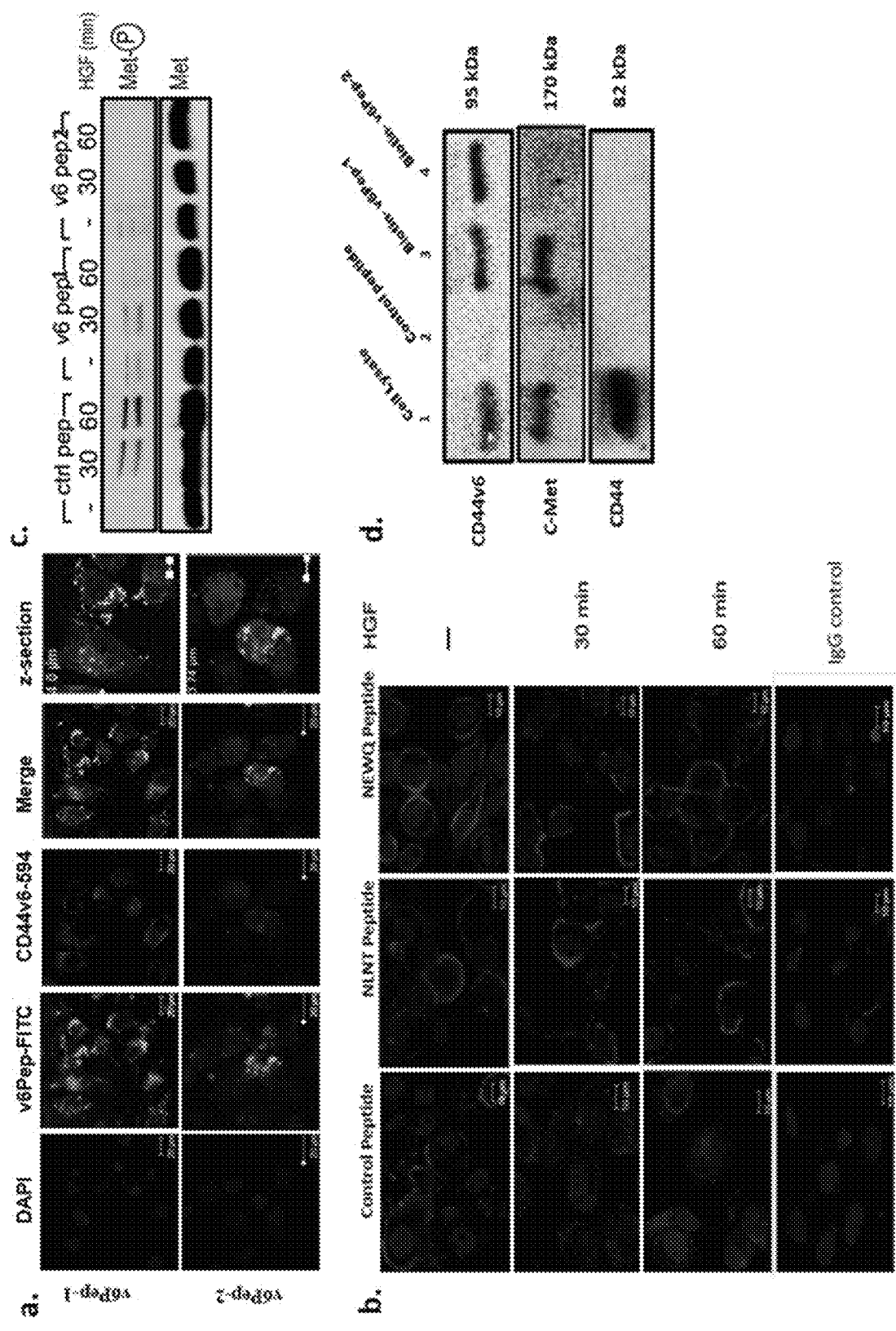
[FIG. 4]

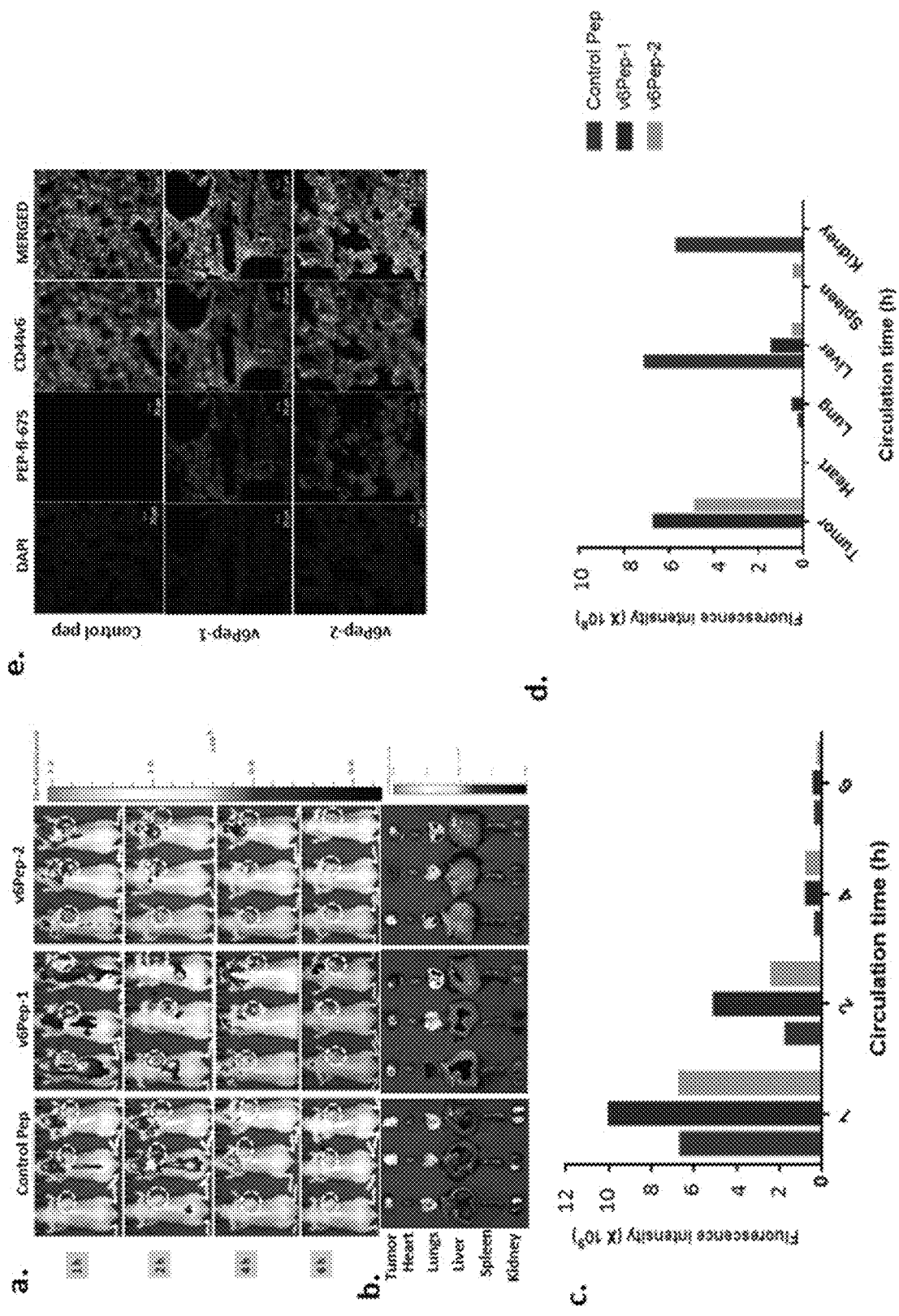
[FIG. 5]

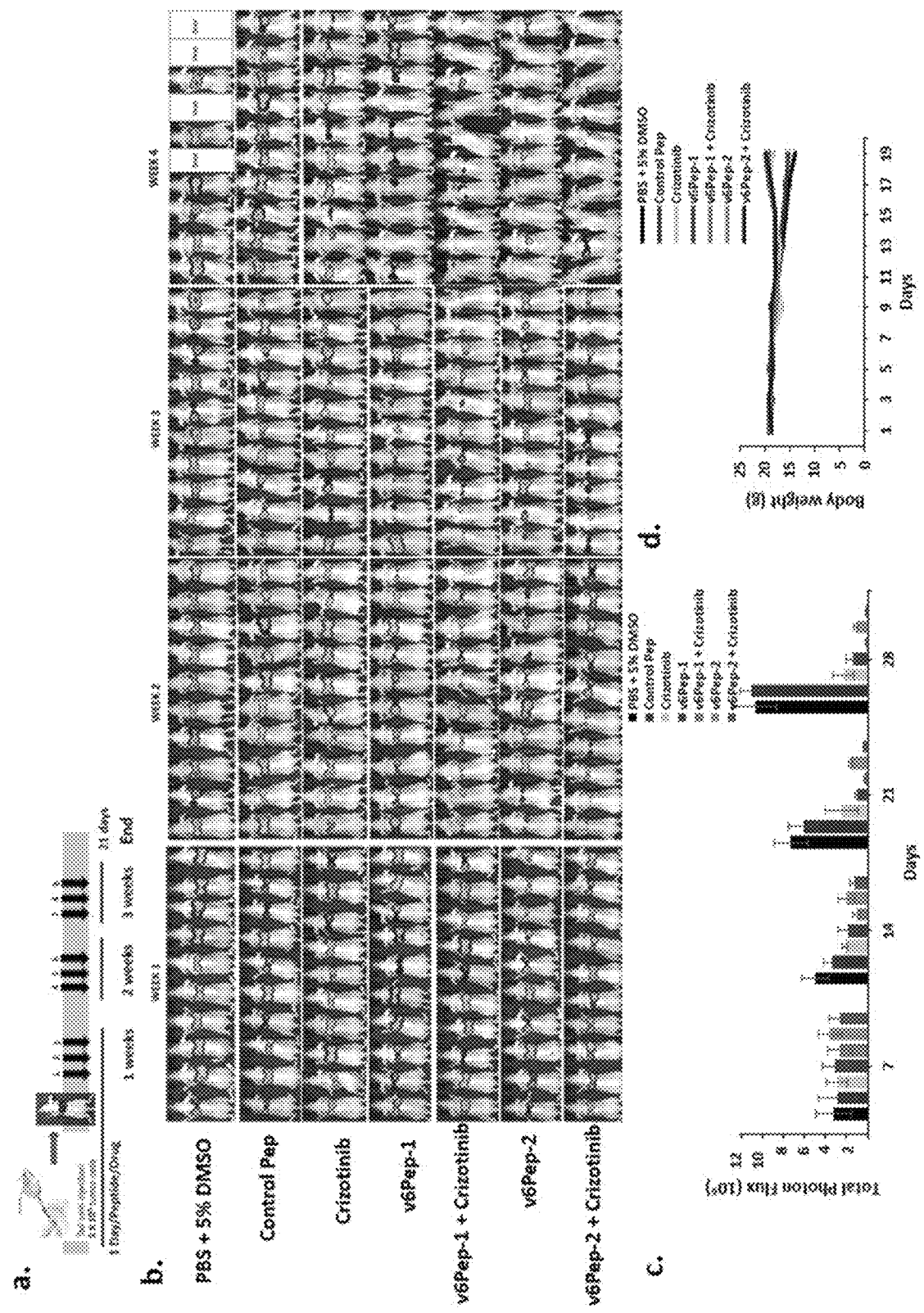
[FIG. 6]

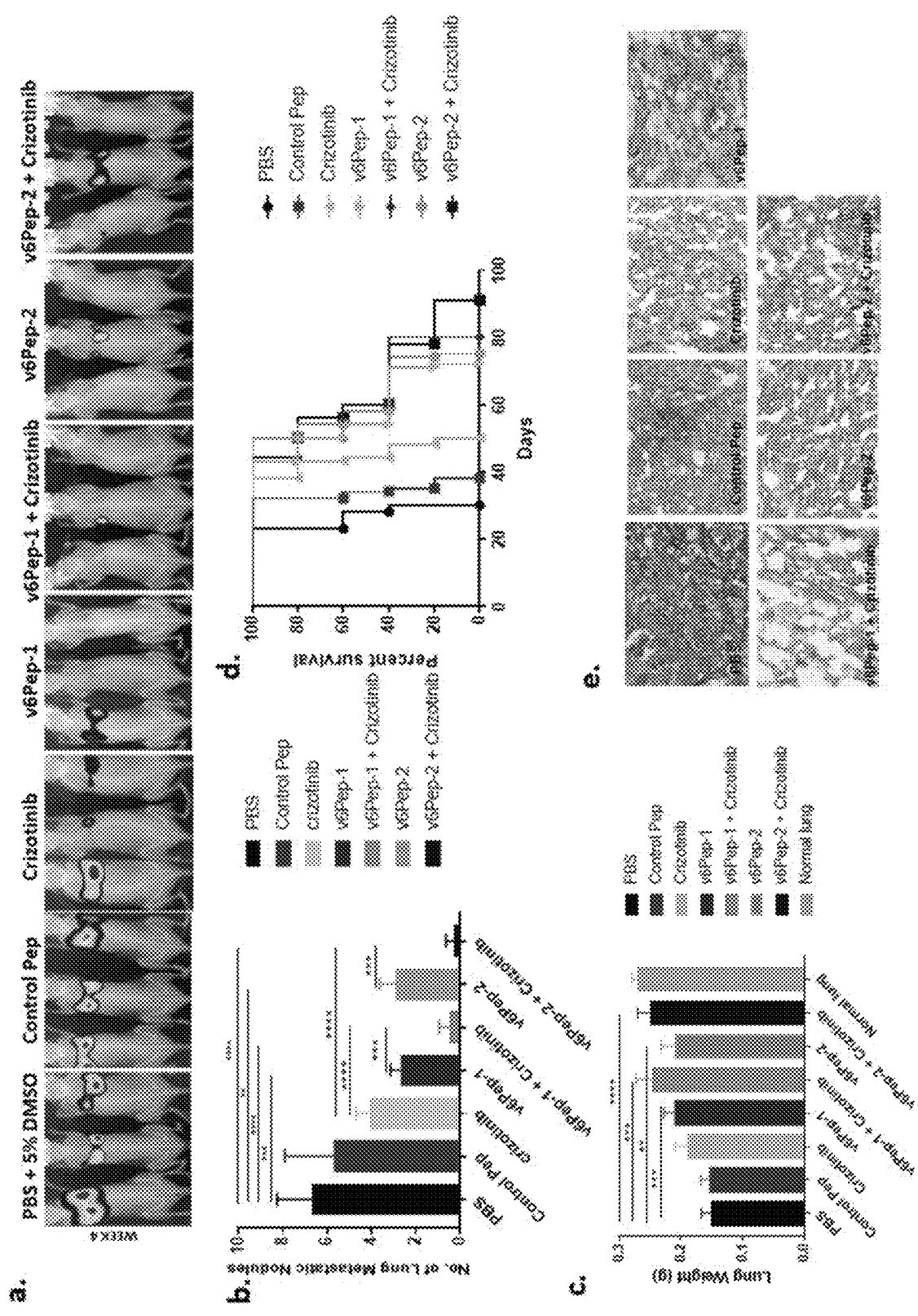
[FIG. 7]

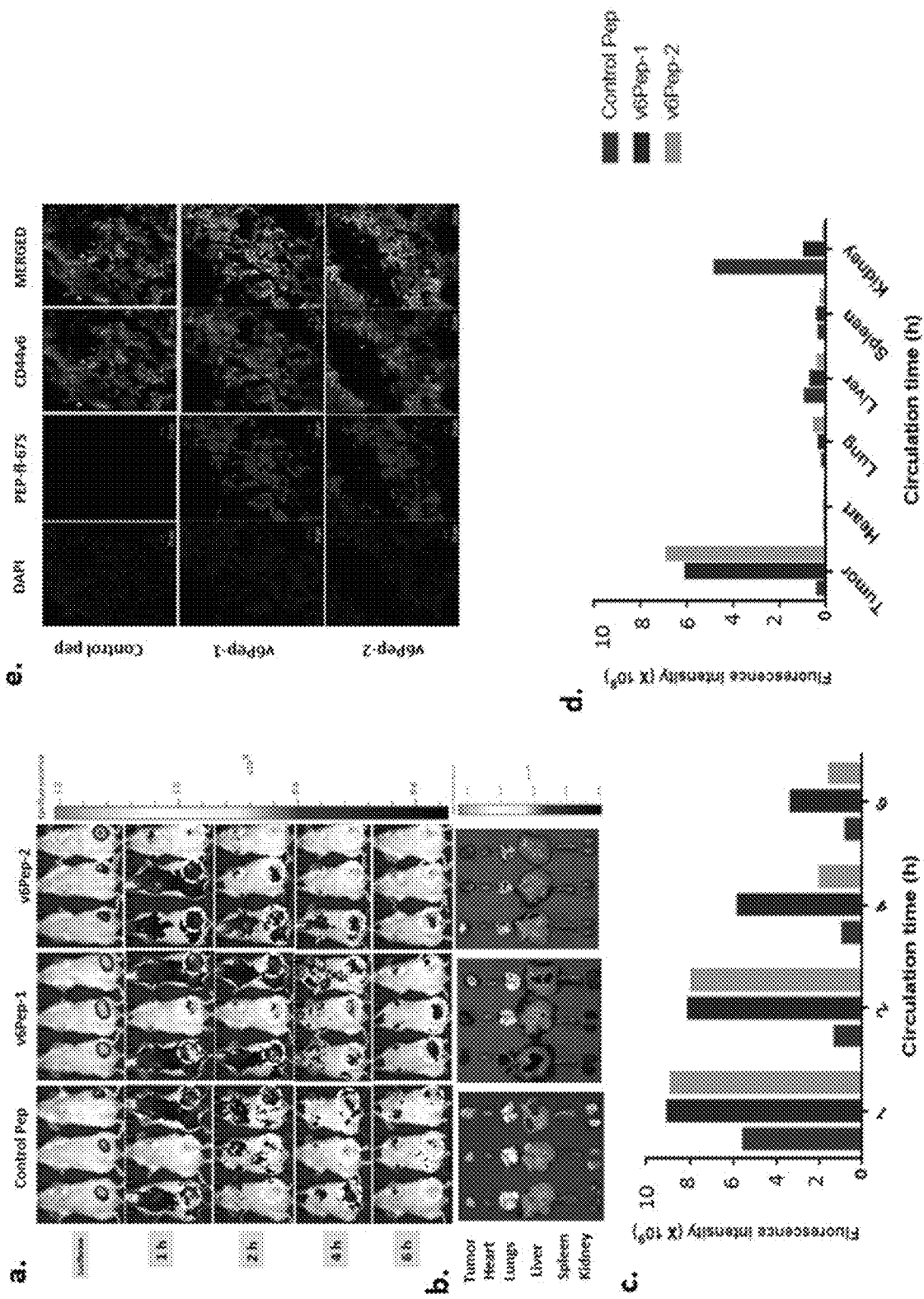
[FIG. 8]

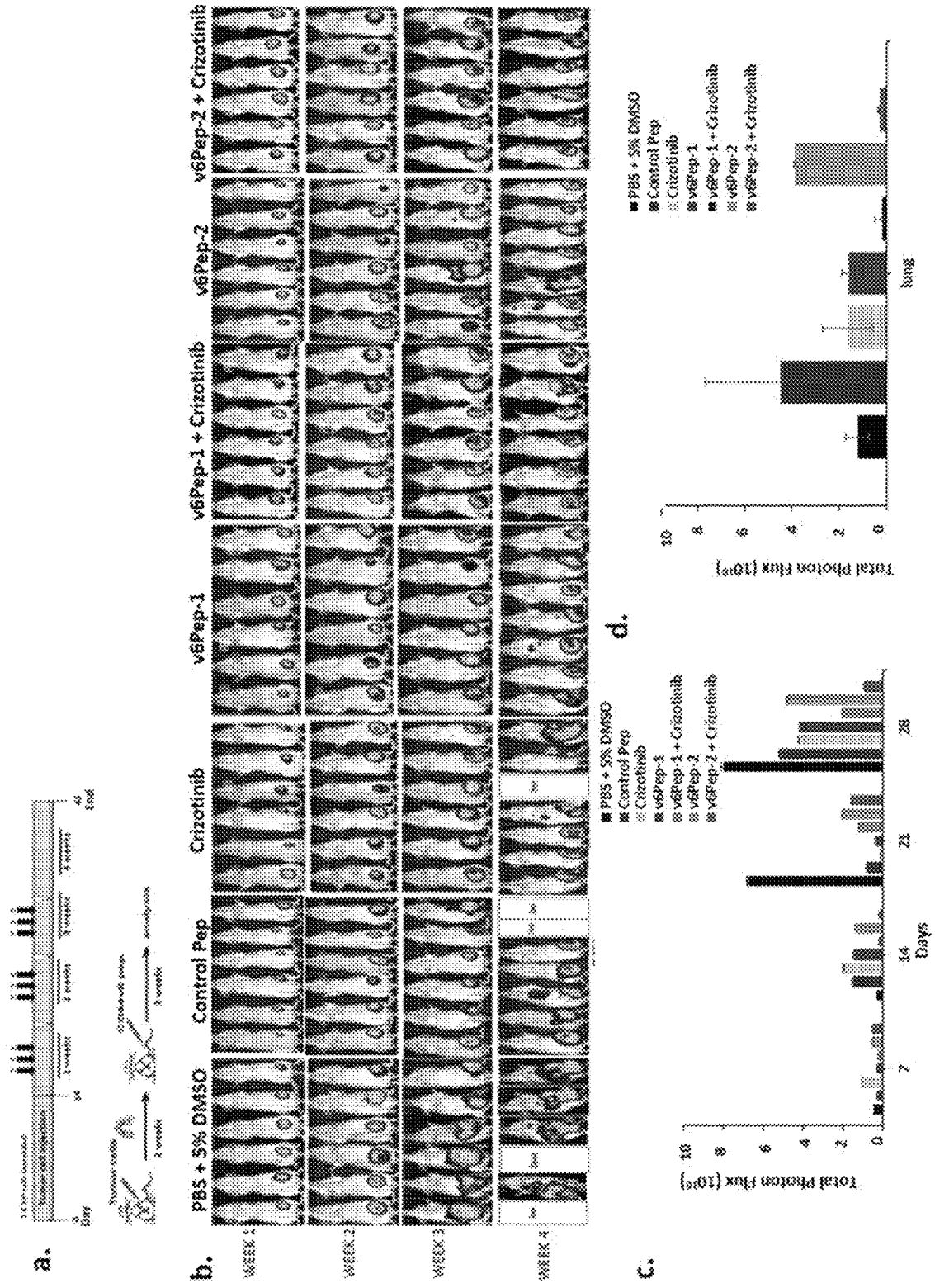
[FIG. 9]

[FIG. 10]
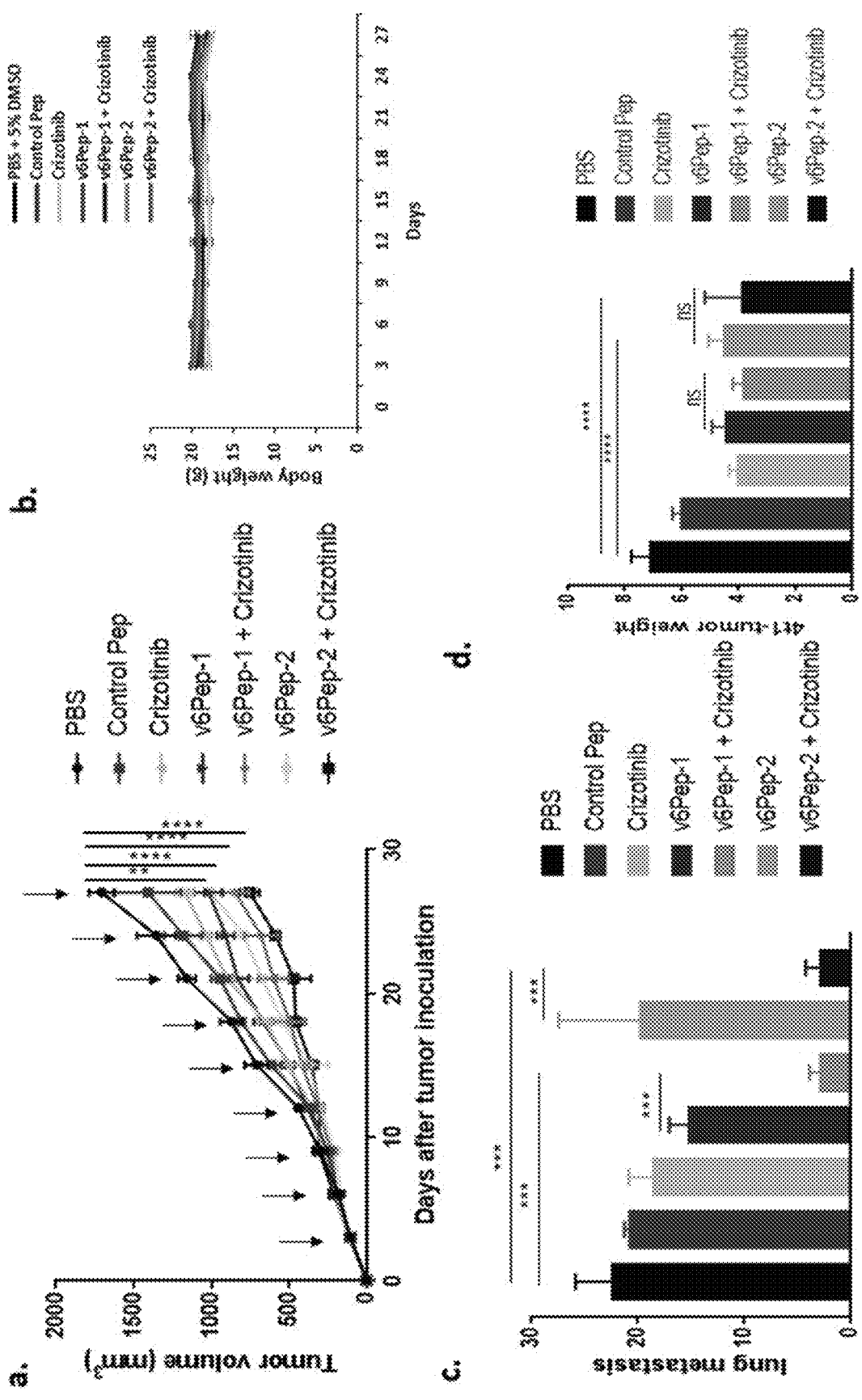

[FIG. 11]
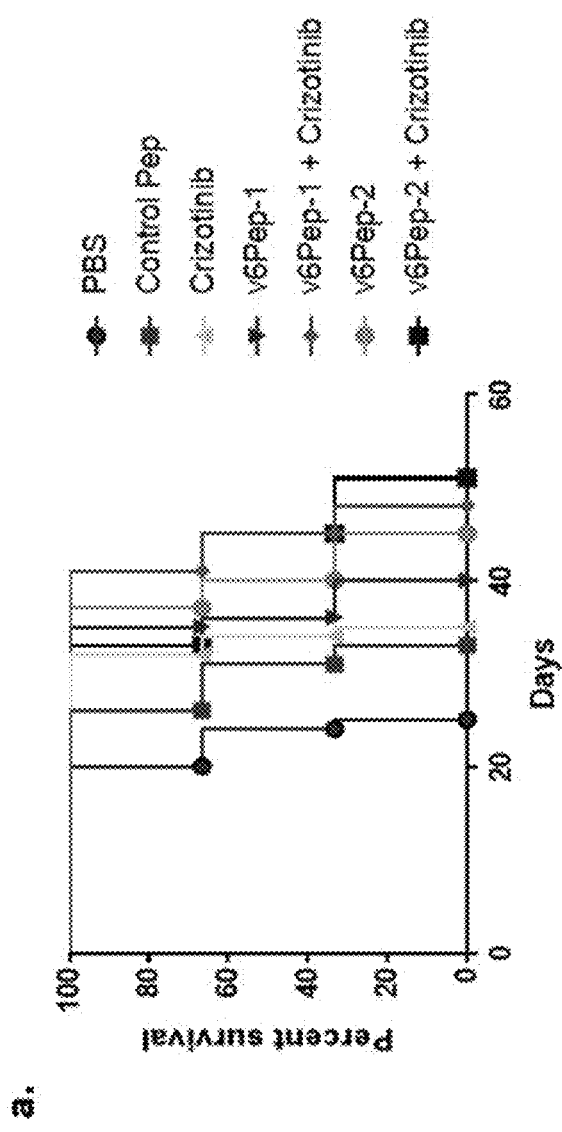
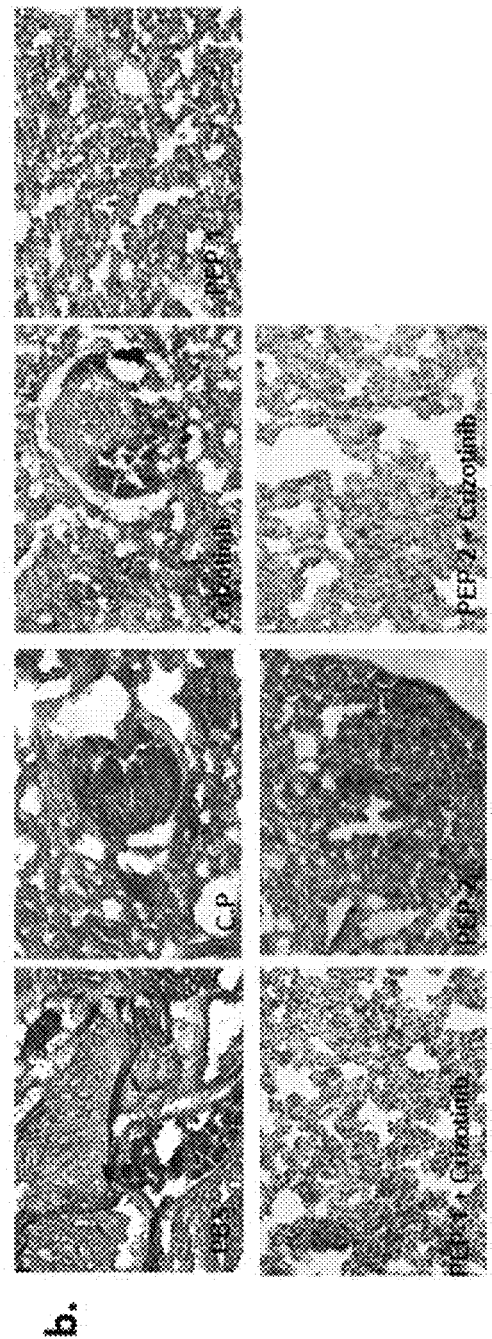

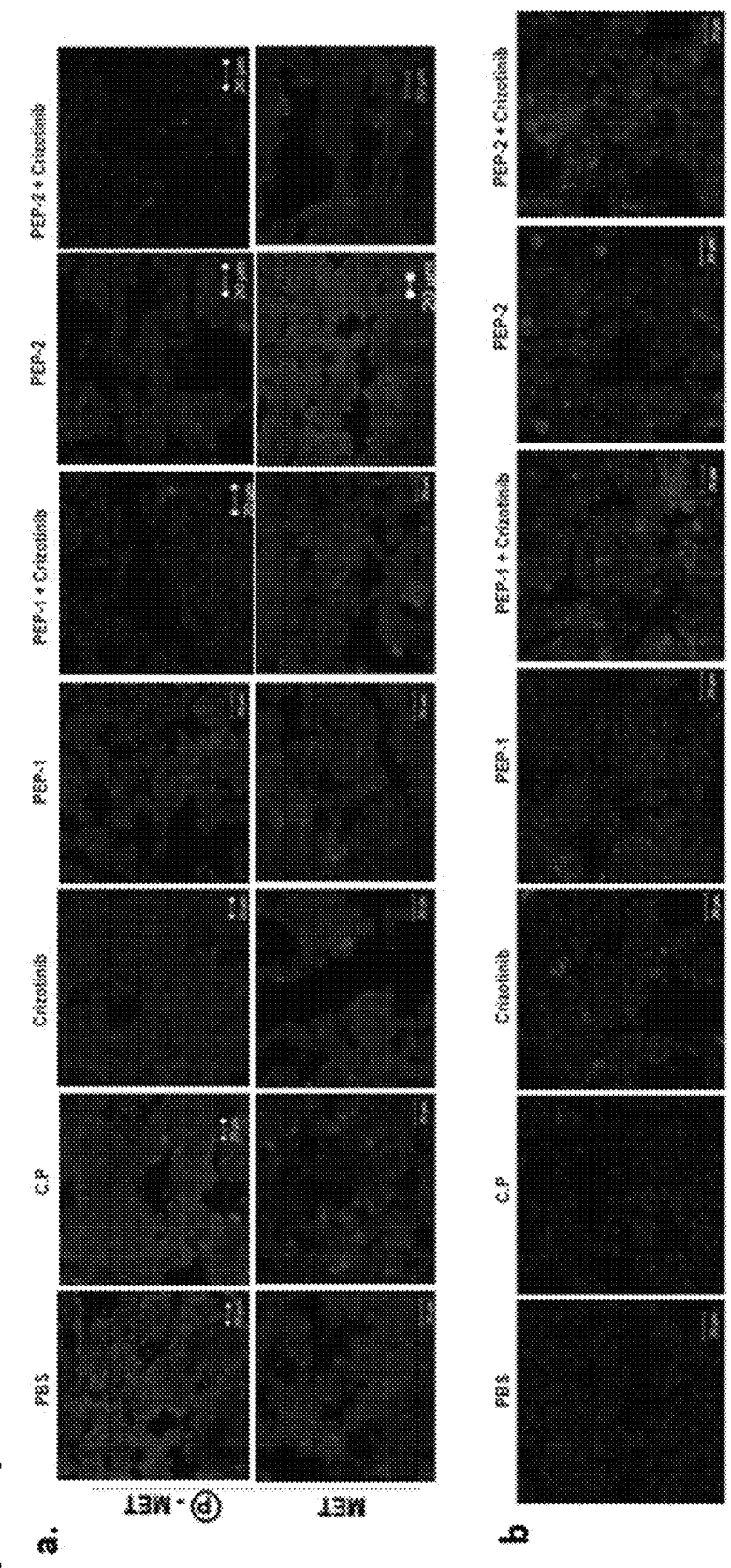
[FIG. 12]

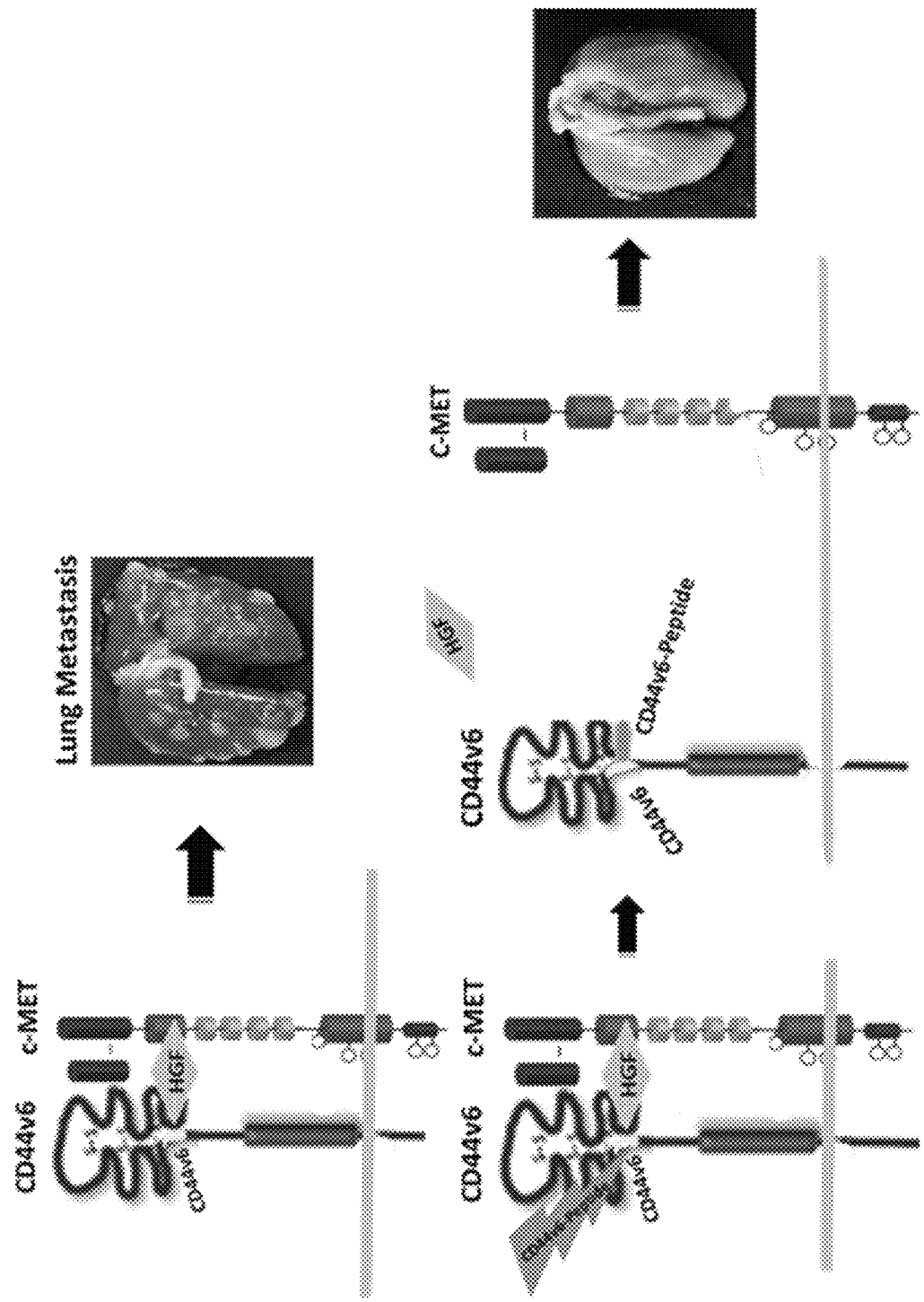
[FIG. 13]

SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Cys Asn Leu Asn Thr Ile Asp Thr Cys
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic peptide

<400> SEQUENCE: 2

Cys Asn Glu Trp Gln Leu Lys Ser Cys
1               5

PEPTIDES FOR BINDING TO CD44V6 AND USE THEREOF

TECHNICAL FIELD

The present invention relates to a peptide bound to CD44v6 and uses for inhibiting cancer metastasis using the same.

BACKGROUND ART

Cancer cells with high metastatic potential and stem cell-like characteristics express the members of the CD44 family of transmembrane glycoproteins, in particular CD44v6 isoform, were shown to be metastatic determinants in aggressive stages of various human cancers. CD44 normally binds to its primary ligand hyaluronic acid (HA) and their molecular weights range from 80 to 200 kDa. The heterogeneity of CD44 proteins is due to alternative splicing of 10 variable exons and additional post-translational modifications. The human CD44 gene is located on the short arm of chromosome 11p13 and chromosome 2 in mice encodes all CD44 proteins. The CD44 chromosome consists of 20 exons, and 10 of them have played a role in splicing called CD44 variants are symbolized by "v" the nomenclature for this is CD44v (1v-10v). These isoforms regulate and participate in cellular differentiation, cell migration and cell behavior by mediating contact between cells and the extracellular matrix and are therefore essential for maintaining tissue integrity. Because of these important functions they are prone to be involved in pathological conditions including tumor progression and metastasis. Specific CD44 variants have been found highly expressed in certain cancer metastatic cells stem cells.

CD44v6 is suggested to be involved in many cancers and shown high frequency of variants CD44v6-v10 reported in metastatic growth, for instance, could indicate that exon v6 boost metastasis of cancer cells, FIG. 13 illustrates the role of CD44v6 peptides in metastatic cancer. Previous study, shown that hepatocyte growth factor (HGF) depends on a CD44 exon v6 containing isoform for the activation of c-Met on epithelial cells by binding of HGF, CD44 isoforms containing the variant exon v6 have been shown to be metastatic determinants. The role of CD44v6 in metastasis result is known to interact with the receptor tyrosine kinase (RTK) c-Met to mediate the action of HGF. The inhibitory action of these v6 peptides offers the promise for a future development of more stable and systemically usable compounds preventing invasion and metastatic spreading of tumor cells by blocking the coreceptor action.

In many carcinomas, the activation and signaling from the c-Met receptor can be blocked by CD44v6-specific antibodies, CD44v6 siRNAs and CD44 variant v6-specific peptides. CD44v6 isoforms play a dual role for c-Met-dependent signaling. The numerous reports are, overall, it seems that a gain of CD44 isoforms correlates with poor prognosis in several human tumors. In high-grade non-Hodgkin's lymphoma expression of the CD44v6 isoform was detected and correlated with poor prognosis. In addition, colon and ovarian cancer expression of CD44v6 and CD44v8-v10 correlates with bad prognosis and can be considered a strong prognosticator in patients. In cervical cancers, a strong expression of CD44v6 and CD44v7-v8 is associated with poor prognosis and in gastric cancer, the expression of CD44v6 and CD44v5 is upregulated. Meanwhile, humanized monoclonal blocking antibodies have been developed and were used in clinical trials, but there is a very high need to develop a peptide capable of binding to and blocking CD44v6.

DISCLOSURE

Technical Problem

The present invention relates to a peptide bound to CD44v6 and uses thereof and provides a peptide specifically bound to CD44v6 comprising the amino acid sequence represented by SEQ ID NO: 1 or SEQ ID NO: 2 and a composition for diagnosing cancer, a pharmaceutical composition for preventing or treating cancer, a health functional food composition for preventing or improving cancer and a composition for drug delivery, comprising the peptide as an active ingredient.

Technical Solution

To order to solve the above problems, the present invention provides a peptide specifically bound to CD44v6, comprising the amino acid sequence represented by SEQ ID NO: 1 or SEQ ID NO: 2.

Also, the present invention provides a polynucleotide encoding the peptide, a recombinant vector comprising the polynucleotide and a transformant transformed with the recombinant vector.

In addition, the present invention provides a composition for diagnosing cancer comprising the peptide as an active ingredient.

Furthermore, the present invention provides a pharmaceutical composition for preventing or treating cancer comprising the peptide as an active ingredient.

In addition, the present invention provides a health functional food composition for preventing or improving cancer comprising the peptide as an active ingredient.

In addition, the present invention provides a composition for drug delivery comprising the peptide as an active ingredient.

Advantageous Effects

The present invention relates to a peptide bound to CD44v6 and uses for inhibiting cancer metastasis using the same, and the peptide of the present invention specifically binds to CD44v6 and inhibits it, thereby inhibiting cancer cell migration and metastasis. The peptides of the present invention selected two peptides (v6Pep-1 and v6Pep-2) that bind well to cells with high expression of human CD44v6 protein using phage peptide display technology and it was confirmed that it interferes with the binding between c-Met and CD44v6 to inhibit cancer cell migration. The peptide of the present invention is relatively stable in serum and shows a high potential as an anticancer treatment agent that suppresses metastasis due to the progression and migration of cancer in the future.

DESCRIPTION OF DRAWINGS

FIGS. 1A-1E show selection of CD44v6-binding peptides using phage display. (A) Immunofluorescence staining of HEK-293 transfected and non-transfected cells with DNA expressing CD44v6 (B) Enrichment of phage titer during screening rounds (C) Relative binding of the CD44v6 peptides in the MDA-MB-231, HELA, 4T1 and MCF-7 through FACS analysis (D) Colocalization of CD44v6 Ab with CD44v6 peptides in CD44v6 expressing cell MDA-MB-231, HELA, 4T1 and CD44v6 non-expressing cell MCF-7 (E) Cell binding affinity of CD44v6 peptides.

FIGS. 2A-2D show CD44v6-specific cellular binding of v6Pep-1 and v6Pep-2. (A) Western blot results to confirm gene knockdown using CD44v6 specific siRNA in MDA-MB-231 cell line (B) Flow cytometry analysis of the fluorescence intensity of cells bound to the FITC-labeled CD44v6 peptide after knockdown of the CD44v6 gene (C) Confocal image analysis of MDA-MB-231 cells stained with v6Pep-1 and v6Pep-2 after CD44v6 antibody reaction (D) Competitive assay results of CD44v6 antibody and CD44v6 peptide in MDA-MB-231 and MCF-7 cells. Data represent the percent binding of the peptide to the cells as the mean±SD of three separate experiments. *p<0.05, **p<0.01 by Students t-test.

FIG. 3 shows inhibition of HGF-induced phosphorylation of c-Met and Erk by v6Pep-1 and v6Pep-2. (a) and (c) Western blot results showing activation of RTKs and Erk in HGF-induced MDA-MB-231 and 4T1 cells (b) and (d) Cell migration analysis in the presence of CD44v6 peptide and control peptide.

FIG. 4 shows the internalization inhibition of HGF-induced c-Met by v6Pep-1 and v6Pep-2 and pull-down of CD44v6. (a) Breast tumor MDA-MB-231 cells were incubated FITC-labeled CD44v6 peptides and further stain with CD44v6 antibody, subjected to the confocal microscopy analysis. (b) Confocal microscopy analysis of CD44v6 peptide according to HGF induction in MDA-MB-231 cells (c) Western blot analysis for phospho-c-Met and c-Met (d) Pull-down assay with the conjugation of Streptavidin with the biotin labelled peptide.

FIG. 5 shows CD44v6 peptides targets CD44v6-expressing human breast tumor cells in vivo (a) In vivo imaging of the tumor homing capacity of v6Pep-1 and v6Pep-2 (b) Ex-vivo imaging of the accumulation of CD44v6 peptides at various organs (c) Quantification of in vivo fluorescence intensities at tumor sites (d) Quantification of the ex vivo fluorescence intensities of tumor and control organs (e) Analysis of the tumor tissue section by a confocal microscope FIG. 6 shows CD44v6 peptide interferes with metastasis of human breast cancer model. (a) Medication schedule. (b) Results of bioluminescence imaging and monitoring of tumor growth. (c) Quantification of total proton flux. (d) Weight during treatment.

FIG. 7 shows CD44v6 peptides interferes with metastasis f human breast cancer model. (a) and (b) Whole body X-ray and bioluminescence imaging results. (c) Lung weight on day 22. (d) Survival rate. (e) Results of H & E staining analysis of frozen lung sections.

FIG. 8 shows the results for a CD44v6 peptide that selectively targets CD44v6-expressing mouse breast tumor cells in vivo. (a) Results of in vivo imaging of tumor homing activity of v6Pep-1 and v6Pep-2. (b) Ex-vivo imaging results of accumulation of CD44v6 peptide in various organs. (c) Result of quantifying the in vivo fluorescence intensity at the tumor location. (d) Results of quantifying ex-vivo fluorescence intensity in tumors and control organs. (e) Results of analysis of tumor tissue sections under confocal microscopy.

FIG. 9 is a result for a CD44v6 peptide blocking metastasis of mouse tumor cells in vivo. (a) An experimental schematic is shown. (b) Results of bioluminescence imaging and monitoring of tumor growth. (c) and (d) Quantitative results of total proton flux in systemic and lung sites.

FIG. 10 shows the results for the CD44v6 peptide blocking metastasis of mouse tumor cells in vivo. (a) Tumor volume change results after tumor inoculation. (b) Weight during treatment. (c) The number of metastatic tumor masses in the lung at the end of treatment. (d) Tumor weight.

FIG. 11 is a result of the CD44v6 peptide blocking metastasis of mouse tumor cells in vivo. (a) It shows the survival rate. (b) Results of H & E staining analysis of frozen lung sections.

FIG. 12 shows the results for the CD44v6 peptide blocking metastasis of mouse tumor cells in vivo. (a) After treatment, it is the result of immunofluorescence staining analysis of primary tumor tissues with phosphorylated c-Met (P-met) and c-Met antibodies. (b) Results of caspase-3 staining analysis of frozen tumor tissue after treatment.

FIG. 13 shows a schematic diagram showing the role of the CD44v6 peptide in metastatic cancer.

BEST MODE

Therefore, the present inventors screened a phage display peptide library with cells that temporarily overexpress CD44v6 in order to identify peptides capable of specifically binding to CD44v6. After multiple screenings, selected phage clones were sequenced. It was confirmed that the two clones among them bind to the CD44v6 expressing cells most selectively, compared to the control clone. The peptides blocked RTK activation, inhibited tumor growth and metastasis expansion in MDA-MB-231 and 4T1 breast cancer mice and significant effects were also observed in combination with crizotinib. As a result, the present inventors have successfully screened peptides which can specifically bind to CD44v6 and effectively inhibit it and confirmed the potential of the peptide as an anticancer treatment and completed the present invention.

The present invention provides a peptide specifically bound to CD44v6 comprising the amino acid sequence represented by SEQ ID NO: 1 or SEQ ID NO: 2. In detail, the peptide may inhibit the phosphorylation of c-Met to block signaling between CD44v6 and c-Met.

The peptides of the invention can be readily prepared by chemical synthesis known in the art (Creighton, Proteins; Structures and Molecular Principles, W. H. Freeman and Co., NY, 1983). Typical methods include liquid or solid phase synthesis, fragment condensation, F-MOC or T-BOC chemistry method (Chemical Approaches to the Synthesis of Peptides and Proteins, Williams et al., Eds., CRC Press, Boca Raton Fla., 1997; A Practical Approach, Atherton & Sheppard, Eds., IRL Press, Oxford, England, 1989), but they are not limited thereto.

In addition, the peptides of the present invention may be prepared by genetic engineering methods. First, a DNA sequence encoding the peptide is synthesized according to a conventional method. DNA sequences can be synthesized by PCR amplification using appropriate primers. Alternatively, DNA sequences may be synthesized by standard methods known in the art, for example, using an automatic DNA synthesizer (e.g., sold by Biosearch or AppliedBiosystems). The fabricated DNA sequence is inserted into a vector comprising one or more expression control sequences (e.g., promoters, enhancers, etc.) that are operatively linked to the DNA sequence and regulate the expression of the DNA sequence, and transformed the host cell with the recombinant expression vector formed therefrom. The resulting transformant is cultured under appropriate medium and conditions to express the DNA sequence, thereby recovering a substantially pure peptide encoded by the DNA sequence from the culture. The recovery can be performed using methods known in the art (e.g., chromatography). In the above, the term "substantially pure peptide" means that the peptide according to the present invention does not substantially contain any other protein derived from the host.

In the present invention, the peptide represented by the amino acid sequence of SEQ ID NO: 1 or SEQ ID NO: 2 has a concept including functional variants thereof. "Functional variant" refers to all similar sequences in which substitution of some amino acids occurs at amino acid positions that do not affect the properties of the peptides of the invention that specifically bind CD44v6.

In addition, the present invention provides a polynucleotide encoding the peptide.

The "polynucleotide" is a polymer of deoxyribonucleotides or ribonucleotides present in single-stranded or double-stranded form. It encompasses RNA genomic sequences, DNA (gDNA and cDNA) and RNA sequences transcribed therefrom, and includes analogs of natural polynucleotides unless otherwise specified.

The polynucleotide includes not only the nucleotide sequence encoding the peptide, but also a sequence complementary to the sequence. The complementary sequence includes not only perfectly complementary sequences, but also substantially complementary sequences.

In addition, the polynucleotide may be modified. Such modifications include addition, deletion or non-conservative substitutions or conservative substitutions of nucleotides. It is interpreted that the polynucleotide encoding the amino acid sequence also includes a nucleotide sequence showing substantial identity to the nucleotide sequence. The substantial identity may be a sequence that exhibits at least 80% homology, at least 90% homology or at least 95% homology when aligning the nucleotide sequence with any other sequence to the maximal correspondence and analyzing the aligned sequence using an algorithm commonly used in the art.

In addition, the present invention provides a recombinant vector comprising the polynucleotide.

In addition, the present invention provides a transformant transformed with the recombinant vector.

In the present invention, "vector" refers to a self-replicating DNA molecule used to carry a clone gene (or another piece of clone DNA).

In the present invention, "recombinant vector" refers to a plasmid, viral vector or other mediator known in the art capable of expressing a nucleic acid inserted in a host cell and the polynucleotide encoding the peptide of the present invention may be operably linked into a conventional expression vector known in the art. Generally, the recombinant vector may include a replication origin capable of proliferating in a host cell, at least one expression control sequences (e.g., promoters, enhancers, etc.) that control expression, a selective marker and a polynucleotide encoding the peptide of the invention operably linked to the expression control sequences. The transformant may be transformed with the recombinant vector.

Preferably, the transformant can be obtained by introducing a recombinant vector comprising a polynucleotide encoding the peptide of the present invention into host cells by a method known in the art, for example, but not limited to, transient transfection, microinjection, transduction, cell fusion, calcium phosphate precipitation, liposome-mediated transfection, DEAE dextran-mediated transfection, polybrene-mediated transfection, electroporation, gene guns and other known methods for introducing nucleic acids into cells (Wu et al., J. Bio. Chem., 267: 963-967, 1992; Wu and Wu, J. Bio. Chem., 263: 14621-14624, 1988).

In addition, the present invention provides a composition for diagnosing cancer comprising the peptide as an active ingredient.

Preferably, the cancer may be CD44v6 overexpressed cancer, and more preferably, the CD44v6 overexpressed cancer is at least one selected from the group consisting of lung cancer, brain tumor, breast cancer, liver cancer, skin cancer, esophageal cancer, testicular cancer, kidney cancer, colorectal cancer, rectal cancer, stomach cancer, kidney cancer, bladder cancer, ovarian cancer, bile duct cancer, gallbladder cancer. uterine cancer, cervical cancer, prostate cancer, head and neck cancer, pancreatic cancer and squamous cell carcinoma, but it is not limited thereto.

In the present invention, "diagnosis" means identifying the presence or characteristics of a pathological condition. For the purposes of the present invention, diagnosis is to confirm the presence or characteristics of cancer.

The diagnosis of cancer using the peptides of the present invention can be diagnosed by reacting the peptides of the present invention with blood, urine or corresponding tissues or cells obtained directly by biopsy to detect their binding.

In addition, in order to easily identify whether or not the peptide of the present invention has been bound to cancer tissue, to detect and to quantify, the peptide of the present invention may be provided in a labeled state. That is, it can be provided by linking (e.g., covalent bond or bridging) to a detectable label. The detectable label may be a chromogenic enzyme (e.g. peroxidase, alkaline phosphatase), radioactive isotopes (e.g. $^{124}$I, $^{125}$I, $^{111}$In, $^{99m}$Tc, $^{32}$P, $^{35}$S), chromophore, luminescent or fluorescent materials (e.g. FITC, RITC, rhodamine, cyanine, Texas Red, fluorescein, phycoerythrin, quantum dots)) and so on.

Similarly, the detectable label may be an antibody epitope, substrate, cofactor, inhibitor or affinity ligand. Such a labeling may be performed during the process of synthesizing the peptide of the present invention, or may be performed in addition to an already synthesized peptide. If a fluorescent material is used as a detectable label, cancer can be diagnosed by fluorescence mediated tomography (FMT). For example, the peptide of the present invention labeled with a fluorescent material can be circulated into the blood to and observed by fluorescence tomography. If fluorescence is observed, it is diagnosed as cancer.

In addition, the present invention provides a pharmaceutical composition for preventing or treating cancer comprising the peptide as an active ingredient.

In addition, the present invention provides a pharmaceutical composition for preventing or treating cancer comprising a peptide and an anticancer agent as an active ingredient.

Preferably, the anticancer agent may be doxorubicin, paclitaxel, vincristine, daunorubicin, vinblastine, actinomycin-D, docetaxel, etoposide, teniposide, bisantrene, homoharringtonine, gleevec (STI-571), cisplatin, 5-fluorouracil, adriamycin, methotrexate, busulfan, chlorambucil, cyclophosphamide, melphalan, nitrogen mustard or nitrosourea, but it is not limited thereto.

Preferably, the cancer may be CD44v6 overexpressed cancer, and more preferably, the CD44v6 overexpressed cancer is at least one selected from the group consisting of lung cancer, brain tumor, breast cancer, liver cancer, skin cancer, esophageal cancer, testicular cancer, kidney cancer, colorectal cancer, rectal cancer, stomach cancer, kidney cancer, bladder cancer, ovarian cancer, bile duct cancer, gallbladder cancer. uterine cancer, cervical cancer, prostate cancer, head and neck cancer, pancreatic cancer and squamous cell carcinoma, but it is not limited thereto.

Preferably, the pharmaceutical composition can inhibit the metastasis of cancer.

The pharmaceutical composition of the present invention may be prepared using a pharmaceutically acceptable and physiologically acceptable adjuvant in addition to the active ingredient, and the adjuvants include excipients, disintegrants, sweeteners, binders, coating agents, expanders, lubricants, slip modifiers or solubilizers such as flavoring agent. The pharmaceutical composition of the present invention may be preferably formulated into a pharmaceutical composition by including at least one pharmaceutically acceptable carriers in addition to the active ingredient for administration. Acceptable pharmaceutical carriers in compositions formulated as liquid solutions, which are sterile and biocompatible, can be used by mixing saline, sterile water, Ringer's solution, buffered saline, albumin injection solution, dextrose solution, maltodextrin solution, glycerol, ethanol and one or more of these components and other conventional additives such as antioxidants, buffers and bacteriostatic agents can be added as necessary. In addition, diluents, dispersants, surfactants, binders and lubricants may be additionally added to formulate into injectable formulations such as aqueous solutions, suspensions, emulsions, pills, capsules, granules or tablets.

Pharmaceutical formulation forms of the pharmaceutical composition of the present invention may be granules, powders, coated tablets, tablets, capsules, suppositories, syrups, juices, suspensions, emulsions, drops or injectable solutions and sustained release formulations of active compounds, etc. The pharmaceutical composition of the present invention can be administered by a conventional manner through intravenous, intraarterial, intraperitoneal, intramuscular, intraarterial, intraperitoneal, intrasternal, transdermal, intranasal, inhalation, topical, rectal, oral, intraocular or intradermal routes. The effective amount of the active ingredient of the pharmaceutical composition of the present invention means an amount required for the prevention or the treatment of the diseases. Accordingly, it can be adjusted according to various factors including the type of disease, the severity of the disease, the type and content of active and other ingredients contained in the composition, the type of formulation and the patient's age, weight, general health status, gender and diet, time of administration, route of administration, secretion rate of the composition, duration of treatment, and drugs used simultaneously, but it is not limited thereto, for example, the composition of the present invention may be administered in a dose of 0.1 ng/kg to 10 g/kg when administered once to several times a day for adults.

In addition, the present invention provides a health functional food composition for preventing or improving cancer comprising the peptide as an active ingredient.

The health functional food composition of the present invention may be provided in the form of powder, granule, tablet, capsule, syrup or beverage and the health functional food composition is used with other foods or food additives in addition to the active ingredient, and can be used as appropriate according to a conventional method. The mixing amount of the active ingredient may be appropriately determined according to its purpose of use, for example, prevention, health or therapeutic treatment.

The effective dose of the active ingredient contained in the health functional food composition may be used in accordance with the effective dose of the pharmaceutical composition, but in the case of long-term intake for health and hygiene purposes or for health control purposes, the effective dose may be less than or equal to the above range, and it is clear that it can be used in an amount above the above range because the active ingredient has no problem in safety.

There are no particular restrictions on the type of the health food, for example, meat, sausage, bread, chocolate, candy, snacks, confectionery, pizza, ramen, other noodles, gums, dairy products including ice cream, various soups, beverages, tea, drinks, alcoholic beverages and vitamin complexes, etc.

In addition, the present invention provides a composition for drug delivery comprising the peptide as an active ingredient.

The peptide according to the present invention can be used as an intelligent drug delivery system that selectively delivers drugs to cancer tissues. If the peptide of the present invention is used in the treatment of cancer in connection with a conventionally known drug, since the drug is selectively delivered to cancer tissue and cancer cells by the peptide of the present invention, it can increase the potency of the drug and at the same time significantly reduce the side effects of the drug on normal tissues.

The drug may be an anticancer agent and the anti-cancer agent that can be linked to the peptide of the present invention can be used without limitation as long as it is used in the treatment of conventional cancer. For example, it includes doxorubicin, paclitaxel, vincristine, daunorubicin, vinblastine, actinomycin-D, docetaxel, etoposide, teniposide, bisantrene, homoharringtonine, gleevec (STI-571), cisplatin, 5-fluorouracil, adriamycin, methotrexate, busulfan, chlorambucil, cyclophosphamide, melphalan, nitrogen mustard and nitrosourea. The linkage between the anticancer agent and the peptide of the present invention can be performed through methods known in the art, such as covalent bonding, crosslinking and the like. To this end, the peptide of the present invention can be chemically modified in a range that does not lose its activity if necessary.

Hereinafter, the present invention will be described in detail with reference to the following examples. The examples are only for describing the present invention in more detail and it is obvious to those skilled in the art that that the scope of the present invention is not limited by these examples embodiments in accordance with the gist of the present invention.

<Experimental Example>

The following experimental examples are intended to provide an experimental example commonly applied to each embodiment according to the present invention.

1. Cell Cultures

Human embryonic kidney cells HEK293 (ATCC) and the human breast cancer cells MDA-MB231 (ATCC) and human pancreatic cancer cells PANC-1 (KCLB) and human cervical cancer cells HELA (ATCC) were grown in Dulbecco modified Eagle medium (DMEM, Invitrogen). MDA-MB-231-Red-Fluc-GFP (Bioware) and 4T1-Red-Fluc-GFP (Bioware) were grown in DMEM supplemented with 10% fetal calf serum (FCS; PAA Laboratories). The MCF-7 in RMPI (Invitrogen) plus 10% FCS. Cells were cultured under sterile conditions in a humidified (85%) incubator with 5% $CO_2$ at 37° C. All experiments were performed in a sterile clean bench. Adherent cells were passaged when they reached about 80% confluency.

2. Antibodies and Other Reagents

The human monoclonal antibody against CD44v6 (VFF-7) was from Santa Cruz, mouse monoclonal CD44v6 (VFF-18) from Abcam, rabbit monoclonal anti-CD44 antibody (AB51037) from Abcam, human monoclonal antibody against CD44 (sc-7297) was from Santa Cruz. The anti-Erk 1 (K-23) antibody from Santa Cruz Biotechnology, and the phospho-Erk phospho-p44/42 and the phospho-Met (D26) the Met (25H2) antibodies were purchased from Cell Signaling Technology (Beverly, UK). Recombinant human HGF (R&D Systems, Wiesbaden, Germany) was activated with 5% FCS overnight.

3. Constructs and Protein Production

The sequence encoding the human CD44v6 was introduced in the CD44v6 expression plasmid pCMV6-AC-GFP from Origene by the PCR subcloning method to remove the GFP reading frame 21 with the forward primer: GGACTTTCCAAAATGTCG and the reverse primer: ATTAGGACAAGGCTGGTGGG. Expression vector were transform to E. coli DH5α and purify the DNA using Mini-Prep Kit (Dokdo-Preparation) to get high amount of DNA for transient transfection.

4. Transfection

HEK293 cells were transiently transfected with Lipofectamine 2000 (Invitrogen) according to the manufacturer's protocol in a 6-well plates. Cells were seeded at a concentration of $2 \times 10^5$ cells in 6-well-plates 24 hours before transfection. To transfect one well, 10 µl Lipofectamine 2000 reagent were diluted in 250 µl DMEM and incubated for 5 min at room temperature. 4 µg of vector DNA were filled up to 250 µl with DMEM without serum and mixed with the Lipofectamine 2000 solution. The mixture was incubated for 20 min at room temperature (in all 500 µl per well). In the meantime old medium on the cells was removed and replaced by 1.5 ml fresh DMEM without serum. 500 µl of DNA-transfection reagent-mixture was applied to the cells before they were transferred to the incubator. After 6 hours incubation, medium was replaced again by pre-warmed growth medium containing serum. Cells were allowed to express the newly inserted protein before the experiments were started.

5. Bio-Panning of T7 Hydrophobic Library for CD44v6 Peptide Screening

A phage peptide library based on T7 415-1 b phage vector displaying CX7C (C, cysteine; X, any amino acid residue) were constructed in according to the manufacturer's manual (Novagen, Madison, Wis.). The phage library had approximately $1 \times 10^9$ plaque forming unit (pfu). In other words, transfected HEK-293 cells (GFP) were plated on 35 mm culture dishes and reached a confluence of 60-70%. The cells were treated with Lipofectamine 2000 (Invitrogen) for transient transfection of HEK-293 cells. Cells were allowed to express CD44v6 the newly inserted protein (GFP) for 24-48 hours before the experiments were started. The phage library of $1 \times 10^9$ pfu (plaque-forming unit) was incubated with transfected HEK 293 cells for 1 h at 4° C., phages bound to the cells were eluted by incubation with 500 µl of BL21 bacteria O.D. 1 for 10 min at room temperature. The eluate was used for titration and the remaining eluted phage incubated in non-transfected cells for 30 min at 4° C.

Thereafter, uncoupled phage were then washed with DMEM containing 10 mg/ml BSA (bovine serum albumin). The phages bound to the cells were eluted by incubation with 500 µl of BL21 bacteria O.D. 1 for 10 min at room temperature. The eluate were used for titration and the remaining eluted phage clones were dissolved in 10 ml LB medium for amplification for next cycle this process was repeated five times in total. After serial dilutions of the eluates were inoculated into E. coli in LB medium incubated for 2 h at 37° C., the titer of the phage was determined by counting the number of colonies.

In order to increase the selectivity of phage clones specific to CD44v6 expressing cells we selected to incubated phage first with transfected cells. The present invention used a direct screening method to use all phage clones in the next round with amplification and phage enrichment methods. Fold reduction of phage clones decreased to $1.9 \times 10^1$ fold, respectively, at 5 rounds. Sequence analysis was performed on a total of 70 clones from the third, fourth and fifth rounds of transfected dish (20 phage clones from third round, 20 phage clones from fourth round, 20 phage clones from fifth round) and 10 phage clones from non-transfected dish to subtract the non-binding phage clones.

DNA and amino acid sequence analysis of a phage clone the DNA inserts of each of the 70 clones collected in the above were sequenced by an automated DNA sequencer (Genotech Inc., Daejeon, Korea) using each primer (Macrogen). The amino acid sequences deduced from the nucleotide sequences were aligned using Clustal W program to find amino acid motifs shared between the consensus sequences or peptides. Some of these peptides were randomly selected and a BLAST search of the NCBI protein database was performed to investigate proteins with high homology to each peptide sequence.

6. Activation of RTKs and Erk

Serum-starved cells (24 hours) were induced with the growth factor HGF (25-50 ng/mL), at 37° C. for 10 min. Where indicated, the cells were treated with a CD44v6 specific peptide or a control peptide (50 µg/ml) at 37° C. for 10 min before induction and cells were washed with ice-cold phosphate-buffered saline (PBS). To detect activated Erk and activated c-Met, cells were lysed in boiling sodium dodecyl sulfate (SDS) sample buffer containing 100 mM dithiothreitol (DTT) and subjected to Western blot analysis using antibodies against phosphorylated Erk and phosphorylated c-Met. The loading control was performed on the same blot, stripped (62.5 mM Tris, pH 6.8, 2% SDS, 0.8% DTT), and probed with the Erk and c-Met antibodies. Blots were stained using the enhanced chemiluminescence system (Thermo Fisher Scientific). Bands in Western blot analysis were quantified with the program ImageJ (National Institutes of Health).

7. Pull Down Assay

Biotinylated CD44v6 peptides was incubated with monomer avidin magnetic beads (Bioclone Inc.) for 30-60 min at room temperature with gentle rotation to be used for peptide pulldown, prior to incubation with cell lysates. Cells were lysed using cell lysis reagent (Thermo scientific) with protease inhibitors. After the first incubation of biotinylated peptide+avidin bead (complex 1) were washed with PBS and complex is incubated with cell lysate for 30-60 min at room temperature with gentle rotation. Bound biotinylated peptide+avidin bead+cell lysate (complex 2) were eluted by 1× blocking buffer/elution buffer for 5-10 min incubation after elution and the elute was subjected to western blot analysis using CD44v6 antibody (Millipore) to pull down the specific protein.

8. Migration Assay

MDA-MB-231 were seeded in 12-well plates at a concentration of $2.5 \times 10^5$ cells per well. After 24 hours, a scratch was made into the confluent cell layer using as sterile pipette tip. The medium was changed and replaced by fresh medium containing growth factor HGF and 25 ng/ml of HGF was treated for induction with the growth factors for 10 min at 37° C. After HGF induction, 5 µg/ml CD44v6 peptide (each) and combination of both peptide (v6Pep-1+v6Pep-2) or 5 µg/ml control peptide were treated for 10 min at 37° C. and pictures of the cells (original magnification, X100) were taken at time intervals from 0 h, 24 h, 48 h, 60 h. The computer program ImageJ was used for quantitative evaluation and the area covered by cells in the scratch was quantified.

9. SiRNA Inhibition

Cells were transfected with a mixture of two CD44v6-specific siRNAs: v6-1: 5'-AGU AGU ACA ACG GAA ATT-39; v62: 59-GGA UAU CGC CAAACA CCC ATT-3' or a pool of nonspecific control siRNA. Control siRNA (50-CUACGCCAAUUUCGU (dTdT) 30) and glyceraldehyde-3 phosphate dehydrogenase (GAPDH) siRNA (50-UGUGAACCAUGAGAAGUA (dTdT)-30) were also purchased from Bioneer, Daejeon, Korea. The transfection was performed using Lipofectamine 2000 (Invitrogen, Karlsruhe, Germany). Two rounds of transfection with an interval of 24 h between were performed. 48 h after the first transfection the cells were serum-starved for 24 h and then subjected to further treatment.

10. Animal Experiments

For animal models, 6-week-old to 8-week-old Balb/c female mice were purchased from Orient Bio. Mice were cared for and maintained in conformance with the Guidelines of the Institutional Animal Care and Use Committee (IACUC) of Kyungpook National University. Tumors were prepared by injecting $1\times10^6$ MDA-MB-231 cells via tail vein to develop lung metastatic model in Balb/c female nude mice and $1\times10^6$ 4T1 cells into the lower left mammary fat pad of Balb/c wild type female mice.

11. Confocal Laser Scanning Microscopy

In order to visualize the distribution of internalized FITC labeled peptides v6Pep-1 and v6Pep-2, MDA-MB-231 cells ($1\times10^5$ cells) were seeded onto 4 well chamber slide. After complete adhesion, the cell culture medium was replaced with fresh medium containing FITC labeled peptides (10 µM) and then the cells were incubated at 37° C. for 1 h and cells were washed with PBS for 3-5 min (thrice) and stained with CD44v6 antibody (Santa cruz), followed by Alexa 594-labeled goat anti-mouse IgG secondary antibody. FITC labelled v6Pep-1 and v6Pep-2 accumulation was observed under a confocal microscope after nuclei were stained with DAPI and mounted on glass slides with the antifade reagent. Localization of FITC-labeled peptides in cells was observed under a confocal microscope (Zeiss, Jena, Germany).

12. In Vivo Biodistribution Imaging

The CD44v6 specific tumor targeting activities of v6Pep1 and v6Pep-2 or control peptide were examined using six-week-old female BALB/c nude mice (weight 20±3 g) housed in a specific pathogen-free environment. Tumors were induced through subcutaneous injections of MDA-MB231 cells ($5\times10^6$ cells) into the right flank. Tumor cells were then left to grow for 2-3 weeks. After tumor volumes had reached approximately 100 mm³, mice (n=3 for each group) were intravenously injected with v6Pep-1, v6Pep-2 and control peptide labeled NIRF via the tail vein. In vivo NIRF imaging was performed using an IVIS Lumina III imaging system (Perkin Elmer, Waltham, Mass.) under inhalational anesthesia. To examine the bio-distribution of v6Pep-1, v6Pep-2 and control peptide In vivo fluorescence images were taken before or after injection at various time points (1, 2, 4, and 4 respectively). Mice were sacrificed after in vivo imaging and tumors and control organs were isolated for further imaging using the IVIS Lumina III imaging system.

13. Ex Vivo Imaging and Immunohistochemistry

To analyze ex vivo organ distribution, animals were euthanized at 6 h post-injection with $CO_2$. All major organs (liver, kidney, spleen, heart, and lung) along with tumor tissues were isolated and washed in PBS and ex vivo fluorescence images were taken using the IVIS Lumina III imaging system. Fluorescence intensity within the region of interest (ROI) of each organs was analyzed. Tumor tissues were further fixed with 4% paraformaldehyde overnight and rapidly frozen. Tissue slices (8-µm thick) were prepared using a cryo-microtome and stained with CD44v6 antibody (Santa Cruz), followed by Alexa 594-labeled goat anti-mouse IgG secondary antibody. Control peptide and v6Pep-1 and v6Pep-2 tumor accumulation was observed under a confocal microscope after nuclei were stained with DAPI.

14. Anti-Tumor Therapy

Tumor-bearing mice were subjected to randomization and grouping when the size of the tumors reached approximately 100 mm³. Each peptide was intravenously injected via the tail vein of mice (14.2 mg/g of body weight, 3 times a week for 3 weeks). Crizotinib was given through orally (25 mg/kg of body weight, three times a week for 3 weeks) based on a previous study. Tumor size was measured using a digital caliper, and tumor volume was calculated using the following formula: Volume=(L×W×H)/2 (L: length, longest dimension, W: width, shorter dimension, parallel to the mouse body, and H: height, perpendicular to the length and width). Mice were checked for tumor ulceration. At the end of the treatment, the mice were sacrificed, and the lung and liver were isolated and checked for metastatic tumor masses.

15. MDA-MB-231 Lung Metastasis Model

MDA-MB231-luc cells ($1\times10^6$ in 0.1 ml PBS) were injected into the lateral tail vein of female nude mice. The mice were then segregated into groups (n=10 per group) based on initial IVIS image. Starting from day 0, mice were administered CD44v6 peptides by intravenously injected via the tail vein of mice (14.2 mg/g of body weight, 3 times a week for 3 weeks). After the last IVIS imaging, mice were euthanized and lung tissues were removed from each mouse for metastatic tumor masses immunohistochemical analyses.

16. Cytotoxicity Analysis

MDA-MB-231 cells ($5\times10^3$ cells/well in 96-well plates) were cultured with v6Pep-1, v6Pep-2 and combination of two peptides (v6Pep-1+ v6Pep-2) having various concentrations in serum free culture Incubation at 37° C. for 4 hours. After replacing the serum-free medium with a culture medium containing 10% FBS, the cells were cultured for 24 hours and 48 hours, and then cytotoxicity was evaluated using CCK-8 analysis (Dojindo, Kumamoto, Japan).

17. Peptide Stability in Serum

To investigate the stability of the peptides (v6Pep1 and v6Pep-2) in serum, blood was collected from mice and coagulated, and then centrifuged twice at 4° C. to obtain serum and then filtered (0.22 µm pore). Peptides (100 µg in 50 µl PBS) were incubated with 50 µl of filtered serum at 37° C. for a predetermined period of time. After 100% dilution of cultured samples, it was fractionated by 18 reversed phase FPLC with linear gradient of acetonitrile (Vydac protein and peptide C18, 0.1% trifluoroacetate in water for equilibrium and 0.1% trifluoroacetate in acetonitrile for elution). To confirm the identity of the peaks from the profile of the C18 reversed phase FPLC, each peak was collected, vacuum dried and analyzed by mass spectrometry (MS) using a MALDI-TOF mass spectrometer.

18. Hematological Parameter Analysis

At the end of the treatment, mouse blood was collected and hematological factors were analyzed by DGMIF (Daegu-Gyeongbuk Medical Innovation Foundation) (Daegu, Korea).

Example 1

Selection of CD44v6-Binding Peptides Using Phage Display

To screen CD44v6-binding peptides, the present inventors first prepared HEK-293 cells transfected with CD44v6-GFP plasmid by transient transfection. HEK-293 transfected cells were stained with CD44 variant 6 antibody to see the colocalization of CD44v6-GFP plasmid (FIG. 1a). After confirmation by immunofluorescence, the transient transfection efficiency was checked with western blotting analysis in two different time intervals 24 h and 48 h, and the transfection was confirmed at each time point as compared to the non-transfected HEK-293 cells. In order to screen CD44v6 specific peptide by direct screening method, the present inventors confirmed that all phage clones in each round showed enrichment output titter, which were significantly increased as compare to non-transfected titter, phage enrich to $3.11 \times 10^1$ fold, respectively, at 5 rounds (FIG. 1b). Twenty phage clones were randomly picked from the third, fourth, and fifth rounds and the peptide-coding DNA inserts of the phage clones were sequenced. Phage clone with high specificity for binding to CD44v6 expressing cells was selected through phage binding ELISA and some of the clones shown binding in several expressing and non-expressing cell lines. Compared to the other phage clones, the clone-1 and clone-2 showed higher levels of binding to the CD44v6 by phage ELISA and phage immunofluorescent staining, which confirm the attachment specificity and effect of the phage clones. Two phage clones were found to have high binding specificity to CD44v6 expressing cells. These two peptide sequences of the clones is as follows; CNLNTIDTC (v6Pep-1, SEQ ID NO: 1), CNEWQLKSC (v6Pep-2, SEQ ID NO: 2), Peptide binding was confirmed by flowcytometry and immunofluorescence, colocalization confirmed that v6Pep-1 to v6Pep-2 specifically bind to CD44 variant 6 expressing cells MDA-MB231, HELA, 4T1 and PANC-1 than non-expressing MCF-7 and HEK-293 non-transfected respectively (FIG. 1c, FIG. 1d). Therefore, MDA-MB-231, 4T1, PANC-1 and MCF-7 tumor cells compared binding affinity with enhanced binding affinity (lower $K_d$ values) (FIG. 1e). The v6Pep-1 and v6Pep-2 did not show specific binding to MCF-7 and it was found to bind specifically to MDA-MB-231, 4T1 and PANC-1.

Example 2

CD44v6-Specific Cellular Binding of v6Pep-1 and v6Pep-2

MDA-MB-231 cells were serum-starved for 24 hours and then subjected to further treatment. SiRNAs v6-1 and v6-2 transfected and kept it for different time interval to achieve the CD44v6 expression inhibition. To confirm the silencing of CD44v6 gene, whole cell extracts were fractionated by SDS-PAGE, and transferred and membrane was treated with 1 μg/ml of CD44v6 and CD44 antibody, incubated overnight at 4° C. After the confirmation of siRNA inhibition by western blot analysis, CD44v6 specific siRNA inhibition was clearly observed at 24 h, 48 h and 72 h, but not seen in wild type CD44 (FIG. 2a). To check the specific binding of peptides to silenced MDA-MB-231, cells were incubated with v6Pep-1, v6Pep-2 (FITC labelled) and the flow cytometry analysis was performed (FIG. 2b). As a result, both peptides showed low binding in MDA-MB-231 and value is calculated to show the mean fluorescence intensity (MFI) of peptides. After silencing of CD44v6 gene, both the peptide shows binding got inhibited, which shows that both the peptides specifically bind to CD44v6. Similarly, after the siRNA (100 nmol) treatment, MDA-MB-231 cells were incubated with FITC labelled v6Pep-1 and v6Pep-2 to check the binding by immunofluorescence staining and both the peptide show negligible binding to cells which confirm that v6Pep-1 and v6Pep-2 specifically bind to the CD44v6 gene (FIG. 2c).

Furthermore, as shown in FIG. 2d, pre-treatment of MDA-MB-231 cells with the anti-CD44v6 blocking antibody significantly reduced the binding of the FITC labelled v6Pep-1 and v6Pep-2 in a dose-dependent manner, while minimal effect was observed in MCF-7 cells. These results suggest that the binding of v6Pep-1 and v6Pep-2 to MDA-MB-231 cells is specifically mediated by CD44v6.

Example 3

Inhibition of HGF-Induced Phosphorylation of c-Met and Erk by v6Pep-1 and v6Pep-2

CD44v6 isoform act as a coreceptor for c-Met in a variety of cancer cell lines and primary cells. The c-Met activation and signaling can be blocked by CD44v6 antibody and peptides. So the present inventors also tested the effect of CD44v6 peptides (v6Pep-1 and v6Pep-2) and a combination of both the peptide (v6Pep1+2) on the activation of c-Met to confirm whether these groups of peptide and combination inhibit or hinder the signaling between CD44v6 and c-Met. In the present invention, MDA-MB-231 and 4T1 cells were serum-starved (24 hours) and were induced with the growth factor HGF (25-50 ng/mL) at 37° C. for 10 min. The cells were treated with a CD44v6 specific peptide or a control peptide (100 ng/ml) at 37° C. for 10 min before induction. To detect activated Erk and activated c-Met, cells were lysed and subjected to Western blot analysis using antibodies against phosphorylated Erk and phosphorylated c-Met. The loading control was performed on the same blot, stripped (62.5 mMTris, pH6.8, 2% SDS, 0.8% DTT), and probed with the Erk and c-Met antibodies. (FIG. 3a and FIG. 3c). MDA-MB-231 cells treated with v6Pep-1, v6Pep-2 5 ug/ml each and combination of both peptide (v6Pep-1+2) 10 μg/ml (5 ug/ml+5 ug/ml) drastically reduced the phosphorylation of c-Met and its downstream target Erk. Also, pre-incubation of HELA cells treated with a CD44v6 peptides reduced the phosphorylation of Met and Erk. Furthermore, to confirm the coreceptor function of CD44v6 and c-Met, MDA-MB-231 were seeded in 12-well plates at a concentration of $2.5 \times 10^5$ cells per well. After 24 hours, a scratch was made into the confluent cell layer using as sterile pipette tip. The medium was changed and replaced by fresh medium containing growth factor HGF for induction with the growth factors, 25 ng/ml of HGF was treated for 10 min at 37° C. After HGF induction, 5 μg/ml CD44v6 peptide (each) and combination of both peptide (v6Pep-1+v6Pep-2) or 5 μg/ml control peptide, was treated for 10 min at 37° C. and then pictures of the cells (original magnification, X100) were taken at time intervals from 0 h, 24 h, 60 h. HGF induced migration and proliferation of cells, leading to closure of scratch in a confluent monolayer, but in the presence of the CD44v6 peptides, this process was strongly inhibited (FIG. 3b and FIG. 3d), whereas a control peptide had no effect.

Example 4

Inhibition of HGF-Induced c-Met Internalization by v6Pep-1 and v6Pep-2

To test the CD44v6 binding-peptide can be internalized into cells, the present inventors evaluated the internalization of FITC labeled peptide. The internalization of the peptide was examined by confocal microscopy after 1 h of incubation of both the peptide in MDA-MB-231 cells at 37° C.

As shown in FIG. 4a, FITC-v6Pep-1 and FITC-v6Pep-2 was internalized into the cells within the range of 1-10 μm and localized to both in cytoplasm. To show that this co-receptor function of CD44v6 for c-Met regulates the internalization of c-Met, the present inventors pre-incubated MDA-MB-231 cells with a CD44v6 peptides or a control peptide prior to induction with HGF and followed the internalization process of c-Met using confocal microscopy (FIG. 4b). In both cases control peptide and CD44v6 peptide treated cells, c-Met was located at the membrane in the absence of HGF. (FIG. 4b), Indeed, strong dotted staining suggesting cytoplasmic localization could be observed at 30 and 60 min of HGF induction. The quantification indicates that most cells have lost the membrane staining. In stark contrast, c-Met stayed at the membrane and almost no internalization was detected upon pre-incubation of MDA-MB-231 cells with the CD44v6 peptides. In the control peptide treated cells, c-Met was internalized after HGF induction. The control peptide has no inhibitory effect. In contrast, the CD44v6 peptide drastically decreased c-Met internalization and c-Met was detected at the membrane at all time points. The quantification clearly indicates that most cells treated with the CD44v6 peptides retained c-Met at the membrane. A Western Blot analysis shows the inhibition of c-Met activation by the CD44v6 peptides (FIG. 4c). Biotinylated peptide+avidin bead+cell lysate (complex 2) were eluted for western blot analysis using CD44v6 antibody to pull down the specific protein. Both CD44v6 and c-MET were pulled down by v6Pep-1 and CD44v6 was pulled down by v6Pep-2 (FIG. 4d). In contrast, wild-type CD44 was not pulled down by either peptide. It indicates that v6Pep-1 and v6Pep-2 have specificity for the CD44 variant 6 protein and v6Pep-1 pulled down c-Met. The above results support that the CD44v6 peptide has high specificity with CD44v6 and its co-receptor c-Met. To examine the cytotoxicity of v6 peptides, MDA-MB-231 and 4T1 cells were incubated with different concentration of the v6Pep-1, v6Pep-2 and combination of both peptide (v6Pep-1+v6Pep-2) for 24 hours. The v6Pep-1, v6Pep-2 and the combination of both peptides did not significantly affect cell viability.

Example 5

CD44v6 Peptides Targets CD44v6-Expressing Human Breast Tumor Cells In Vivo

As an experiment for monitoring and imaging using a peptide probe, MDA-MB-231 cells were subcutaneously xenograft into immunodeficient female nude mice to grow tumors, and animal models for experiments were constructed. Tumor xenograft mice were generated by implanting an MDA-MB-231 cell suspension ($5\times10^6$ cells) with PBS subcutaneously into the right flank of 5-week-old BALB/c nude female mice. When tumor size reached a volume of approximately 100-200 mm$^3$, mice were anesthetized and injected with FPR 675-labeled v6Pep-1 (n=3) and v6Pep-2 (n=3), control (n=3) intravenously. In vivo fluorescence images were taken before or after injection at various time points (1, 2, 4 and 6 h, respectively) with flamma 675 was injected at the same concentration and method. NIRF imaging signals were scanned and acquired using an IVIS imaging system (Caliper Life Sciences, Massachusetts). In vivo image showed different time intervals of v6Pep-1 and v6Pep-2 readily localized to tumor tissue in MDA-MB-231 xenograft mice and persisted longer than 6 h (FIG. 5a and FIG. 5c). On the other hand, control peptide showed no accumulation at tumor sites with high non-specific tissue localization. Thus, despite having nearly similar pharmacokinetic properties, v6Pep-1 and v6Pep-2 displayed superior tumor accumulation compared to control peptide. Ex vivo fluorescence images of excised tumor and organs collected at 6 h post-injection. All major organs (liver, kidney, spleen, heart, and lung) along with tumor tissues were isolated and washed in PBS and ex vivo fluorescence images were taken (n=3) with FPR-675 fluorophore excitation at 675 nm and emission at 698 nm. Fluorescence intensity within the region of interest (ROI) of each organ was analyzed. Fluorescence intensity in target tumors shows high accumulation of v6Pep-1 and v6Pep-2-injected mice compared to control peptide (FIG. 5b and FIG. 5d). Higher accumulation in the liver and kidney was observed in control peptide-injected mice compared to v6Pep-1 and v6Pep-2 along with negligible levels in the lung, liver. In addition, immunohistochemical examination of tissues demonstrated that the v6Pep-1 and v6Pep-2 co-localized with CD44v6 at tumor tissues, as detected by staining with an anti-CD44v6 antibody. Consistent with the in vivo and ex vivo results, immunohistological examination of tumor tissue revealed that v6Pep-1 and v6Pep-2 was highly confined to CD44v6 overexpressing tumor tissue (FIG. 5e) than the control peptide.

Example 6

CD44v6 Peptide Interferes with Metastasis of Human Breast Cancer Model

Next, the present inventors tested the antitumor efficacy of v6Pep-1 and v6Ppe-2 and the combination with a c-Met inhibitor compound, crizotinib in MDA-MB-231 tumor model. CD44v6 Peptides was stable without degradation for at least 24 hours in the presence of serum. Systemic administration of v6Pep-1+ crizotinib and v6 Pep-2+ crizotinib significantly inhibited metastasis and with the treatment with v6Pep-1, v6 Pep-2 and crizotinib alone also shows inhibited metastatic growth compared with the saline and control peptide treated group (FIG. 6b).

Quantification of total photon flux (the number of photons/second, p/s) at whole body and lung regions the flux was drastically decreased upon treatment shown in (FIG. 6c). In addition, X-ray with bioluminescence imaging of whole body of each group showed similar results (FIG. 7a). To evaluate the biological safety of v6Pep-1 and v6Ppe-2 with crizotinib, the present inventors monitored the changes in body weight during the continuous injection and treatment process (FIG. 6d). During therapy, there was little change in body weight in mice according to the injection of These CD44v6 peptides. In addition, various blood biochemistry and hematology parameters after therapy was measured, but there was no big difference. In addition, the inhibited metastatic growth in treated group shows negligible metastatic nodules or micro nodules compare to PBS (saline) or single treated group, (FIG. 7b). Lung weight was measured in the PBS treatment group, which showed a difference in weight compared to normal lung weight. This suggested that increase in metastatic nodules and decrease in lung weight lead to less survival rate than compare to CD44v6 peptides treated group (FIG. 7c and FIG. 7d). H &

E staining of frozen lung tissue showed normal lung histology in combination group than control or alone group (FIG. 7e).

Example 7

CD44v6 Peptides Selectively Targets CD44v6-Expressing Mouse Breast Tumor Cells In Vivo As an experiment for monitoring and imaging using a peptide probe, tumor cells were subcutaneously xenograft into immunodeficient female nude mice to grow tumors, and animal models for experiments were constructed. Tumor xenograft mice were generated by implanting a 4T1 cell suspension ($5 \times 10^6$ cells) with PBS subcutaneously into the mammary fat pad of 5-week-old BALB/c wild type female mice.

When tumor size reached a volume of approximately 100-200 mm$^3$, mice were anesthetized and injected with FPR 675-labeled v6Pep-1 (n=3) and v6Pep-2 (n=3), control (n=3) intravenously. In vivo fluorescence images were taken before or after injection at various time points (1, 2, 4 and 6 h, respectively) with flamma 675 was injected at the same concentration and method. NIRF imaging signals were scanned and acquired using an IVIS imaging system (Caliper Life Sciences, Massachusetts). In vivo image showed different time intervals of v6Pep-1 and v6Pep-2 localized to tumor tissue in 4T1 orthotopic mice and persisted longer than 6 h (FIG. 8a and FIG. 8c). On the other hand, control peptide showed no accumulation at tumor sites with high non-specific tissue localization.

Thus, despite having nearly similar pharmacokinetic properties, v6Pep-1 and v6Pep-2 displayed superior tumor accumulation compared to control peptide. This clearly indicates that improved pharmacokinetic properties were not a crucial factor in determining the tumor targeting activity of peptides. Ex vivo fluorescence images of excised tumor and organs collected at 6 h post-injection. All major organs (liver, kidney, spleen, heart, and lung) along with tumor tissues were isolated and washed in PBS and ex vivo fluorescence images were taken (n=3) with FPR-675 fluorophore excitation at 675 nm and emission at 698 nm. Fluorescence intensity within the region of interest (ROI) of each organ was analyzed. Fluorescence intensity in target tumors shows high accumulation of v6Pep-1 and v6Pep-2-injected mice compared to control peptide (FIG. 8b and FIG. 8d). Higher accumulation in the liver and kidney was observed in control peptide-injected mice compared to v6Pep-1 and v6Pep-2 along with negligible levels in the lung, liver. In addition, immunohistochemical examination of tissues demonstrated that the v6Pep-1 and v6Pep-2 were co-localized with CD44v6 at tumor tissues, as detected by staining with an anti-CD44v6 antibody. Consistent with the in vivo and ex vivo results, immunohistological examination of tumor tissue revealed that v6Pep-1 and v6Pep-2 was highly confined to CD44v6 overexpressing tumor tissue than the control peptide (FIG. 8e).

Example 8

CD44v6 Peptides Blocks Metastasis of Mouse Tumor Cells In Vivo

The present inventors tested the antitumor efficacy of v6Pep-1 and v6Ppe-2 and the combination with crizotinib in 4T1 tumor model. Systemic administration of v6Pep-1+ crizotinib and v6Pep-2+ crizotinib significantly inhibited metastasis but with the treatment with v6Pep-1, v6Pep-2 and crizotinib alone slightly inhibited tumor and metastatic growth compared with the saline treated group (FIG. 9b). As a result of quantification of total photon flux (the number of photons/second, p/s) at whole body and lung regions, the flux was significantly reduced in the treatment group (FIG. 9c and FIG. 9d). In vivo anti-tumor activity was further evaluated in 4T1 orthotopic mice models. In relevant with the biodistribution and pharmacokinetic results, in vivo therapy was started by administrating 14.2 mg/kg thrice a week via intravenous injection of CD44v6 peptides and 25 mg/kg crizotinib thrice a week orally. Intravenous administration of v6Pep-1+ crizotinib and v6Pep-2+ crizotinib inhibited tumor growth dramatically, whereas a slight but insignificant reduction in tumor growth was detected in the alone treated group in 4T1 bearing mice (FIG. 10a). On the other hand, tumors in the PBS and control peptide treated groups grew more aggressively, reaching a size of 1,409 mm$^3$ after 28 days. Slight reduction of tumor volume was observed in CD44v6 peptides or crizotinib alone treated mice, as result of enhanced tumor targeting based on the highly expressed CD44v6 on surface of cancer cells. The tumor weight excised at the end of therapy was significantly reduced compared to the control (FIG. 10d).

Furthermore, the metastatic growth inhibited in treated group showed negligible metastatic nodules or micro nodules compared to PBS (saline) or single treated group (FIG. 10c). To evaluate the biological safety of v6Pep-1 and v6Ppe-2 with crizotinib, the present inventors monitored the changes in body weight during the treatment process and continuous injection of CD44v6 peptides and drug during therapy did not change body weight of mice (FIG. 10b). In addition, various analysis for blood biochemistry and hematology parameters was performed after therapy, there was no big difference. Survival rate measured in PBS and control peptide showed less survival than peptide and crizotinib treated group (FIG. 11a). H & E staining of frozen lung tissue showed normal lung histology in combination group than control or alone group (FIG. 11b).

The c-MET activation in tumor using phospho-c-Met staining was completely inhibited by CD44v6 peptide with crizotinib combination treatment, but only partially inhibited by single treated group (FIG. 12a). Further, caspase 3 detected more apoptotic cells in tumor tissue of the v6Pep-1+ crizotinib and v6Ppe-2+ crizotinib treated group but not in the control (FIG. 12b). These results further validated that v6Pep-1+ crizotinib and v6Pep-2+ crizotinib specifically to the tumor site by penetrating various biological barriers as well as facilitated entry into cells and subsequently inducing massive apoptosis.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A peptide for specifically binding to CD44v6, comprising an amino acid sequence represented by SEQ ID NO: 1 or SEQ ID NO: 2.

2. The peptide of claim 1, wherein the peptide specifically inhibits phosphorylation of c-Met to block signaling between CD44v6 and c-Met.

3. A method for diagnosing cancer, comprising: obtaining a biological sample comprising CD44v6 from a patient; contacting the biological sample with the peptide of claim 1; and determining whether or not the peptide is bound to CD44v6.

4. The method of claim 3, wherein the cancer is CD44v6 overexpressed cancer.

5. The method of claim 4, wherein the CD44v6 overexpressed cancer is at least one selected from the group consisting of lung cancer, brain tumor, breast cancer, liver cancer, skin cancer, esophageal cancer, testicular cancer, kidney cancer, colorectal cancer, rectal cancer, stomach cancer, kidney cancer, bladder cancer, ovarian cancer, bile duct cancer, gallbladder cancer, uterine cancer, cervical cancer, prostate cancer, head and neck cancer, pancreatic cancer and squamous cell carcinoma.

6. A method for treating cancer, comprising a step of administering to a subject in need thereof a pharmaceutical composition comprising the peptide of claim 1 as an active ingredient.

7. The method for treating cancer of claim 6, wherein the cancer is CD44v6 overexpressed cancer.

8. The method for treating cancer of claim 7, wherein the CD44v6 overexpressed cancer is at least one selected from the group consisting of lung cancer, brain tumor, breast cancer, liver cancer, skin cancer, esophageal cancer, testicular cancer, kidney cancer, colorectal cancer, rectal cancer, stomach cancer, bladder cancer, ovarian cancer, bile duct cancer, gallbladder cancer, uterine cancer, cervical cancer, prostate cancer, head and neck cancer, pancreatic cancer and squamous cell carcinoma.

9. The method for treating cancer of claim 6, wherein the pharmaceutical composition inhibits metastasis of cancer.

* * * * *